US008268575B2

(12) United States Patent (10) Patent No.: US 8,268,575 B2
Imai et al. (45) Date of Patent: Sep. 18, 2012

(54) NAD BIOSYNTHESIS SYSTEMS

(75) Inventors: Shin-Ichiro Imai, St. Louis, MO (US);
Javier R. Revollo, St. Louis, MO (US);
Andrew A. Grimm, St. Louis, MO (US)

(73) Assignee: Washington University, Saint Louis, MO (US)

( * ) Notice: Subject to any disclaimer, the term of this patent is extended or adjusted under 35 U.S.C. 154(b) by 553 days.

(21) Appl. No.: 11/575,605

(22) PCT Filed: Sep. 20, 2005

(86) PCT No.: PCT/US2005/033611
§ 371 (c)(1),
(2), (4) Date: Dec. 5, 2008

(87) PCT Pub. No.: WO2006/041624
PCT Pub. Date: Apr. 20, 2006

(65) Prior Publication Data
US 2009/0246803 A1 Oct. 1, 2009

Related U.S. Application Data

(60) Provisional application No. 60/611,799, filed on Sep. 20, 2004, provisional application No. 60/645,174, filed on Jan. 20, 2005.

(51) Int. Cl.
*C12P 19/36* (2006.01)
*C07H 21/04* (2006.01)
*G01N 33/573* (2006.01)
*C12N 15/63* (2006.01)
*C12N 5/10* (2006.01)

(52) U.S. Cl. ........ 435/7.8; 435/29; 435/320.1; 435/325; 435/90; 536/23.1

(58) Field of Classification Search ........................ None
See application file for complete search history.

(56) References Cited

OTHER PUBLICATIONS

Zhang et al. Structural Characterization of a Human Cytosolic NMN/NaMN Adenylyltransferase and Implication in Human NAD Biosynthesis..Journal of Biological Chemistry 2003, vol. 278, No. 15, 13503-13511.*
Rongvau e! al. Pre-B-Cell colony-enhancing factor, whose expression is up-regulated in activated lymphocytes, is a nicotinamide phosphoribosyltransferase, a cytosolic enzyme involved in NAD biosynthesis. European Journal of Immunology 2002, vol. 32, p. 3225-3234.*
Walker et al Biochemical Education vol. 20, Issue 1, pp. 42-43, Jan. 1992.*
Magni et al. Enzymology of NAD+ homeostasis in man. Cell Molecular Life Science 61 (2004)19-34.*
Raffaelli NIdentification of a novel human nicotinamide mononucleotide adenylyltransferase.Biochem Biophys Res Commun. Oct. 4, 2002;297(4):835-42.*
Su-Ju Lin Nicotinamide adenine dinucleotide, a metabolic regulator of transcription, longevity and disease in Current Opinion in Cell Biology 2003.*
Martin et al (Identification of a Plasmid-Encoded Gene from *Haemophilus ducreyi* which Confers NAD Independence. Journal of Bacteriology, Feb. 2001, vol. 183, No. 4 p. 1168-1174.*
Revollo et al., "Nampt/PBEF/Visfatin Regulates Insulin Secretion in Beta Cells as a Systemic NAD Biosynthetic Enzyme," 2007, Cell Metab, 6(5):363-375.
Office action issued in U.S. Appl. No. 11/542,790, dated Mar. 17, 2009, 10 pages.
Anderson, "Manipulation of a Nuclear NAD+ Salvage Pathway Delays Aging without Altering Steady-state NAD+ Levels*," 2002, J Biol Chem, 277/21, pp. 18881-18890.
Anderson, "Nicotinamide and PNC1 Govern Lifespan Extension by Calorie Restriction in *Saccharomyces cerevisiae*," 2003, Nature, 423, pp. 181-185.
Araki, "Increased Nuclear NAD Biosynthesis and SIRT1 Activation Prevent Axonal Degeneration," 2004, Science, 305, pp. 1010-1013.
Balducci, "Assay Methods for Nicotinamide Mononucleotide Adenylyltransferase of Wide Applicability," 1995, Anal Biochem, 228, pp. 64-68.
Bernofsky, Physiologic Aspects of Pyridine Nucleotide Regulation in Mammals, 1980, Mole Cell Biochem, 33, 135-143 Abstract Only.
Blander, "The Sir2 Family of Protein Deacetylases," 2004, Annu Rev Biochem, 73, pp. 417-435.
Brunet, "Stress-Dependent Regulation of FOXO Transcription Factors by the SIRT1 Deacetylase," 2004, Science, 303, 2011-2015.
Cohen, "Calorie Restriction Promotes Mammalian Cell Survival by Inducing the SIRT2 Deacetylase," 2004, Science, 305, 390-392.
Conforti, "A Ufd2/D4Cole1e Chimeric Protein and Overexpression of Rbp7 in the Slow Wallerian Degeneration (Wlds) Mouse, "2000, PNAS, 97/21, pp. 11377-11382.
Denu, "Linking Chromatin Function with Metabolic Networks: Sir2 Family of NAD+-dependent Deacetylases," 2003, Trends Biochem Sci, 28/1, 41-48.
Emanuelli, "Three-Minute High-Performance Liquid Chromatographic Assay for NMN Adenylyltransferase Using a 20-mm-long Reversed-Phase Column," 1996, J Chromatography, 676, pp. 13-18.
Emanuelli, "Molecular Cloning, Chromosomal Localization, Tissue mRNA Levels, Bacterial Expression, and Enzymatic Properties of Human NMN Adenylyltransferase*", 2001, J Biol Chem, 276/1, pp. 406-412.
Evans, "LC/MS Analysis of NAD Biosynthesis Using Stable Isotope Pyridine Precursors," 2002, Anal Biochem, 306, pp. 197-203.
Fernando, "Human Homologue of a Gene Mutated in the Slow Wallerian Degeneration (C57BL/Wlds) Mouse," 2002, Gene, 284, pp. 23-29.
Fulco, "Sir2 Regulates Skeletal Muscle Differentiation as a Potential Sensor of the Redox State," 2003, Mol Cell, 12, pp. 51-62.
Gallo, "Nicotinamide Clearance by Pnc1 Directly Regulates Sir2-Mediated Silencing and Longevity," 2004, Mol Cell Biol, 24/3, pp. 1301-1312.

(Continued)

*Primary Examiner* — Kagnew H Gebreyesus
(74) *Attorney, Agent, or Firm* — Zackson Law LLC; Saul L. Zackson

(57) ABSTRACT

The present invention generally relates to a nicotinamide adenine dinucleotide (NAD) biosynthesis system and methods of screening for NAD biosynthesis effectors. Among the various aspects of the present invention is the provision of an in vitro-reconstituted mammalian NAD biosynthesis system that can be used for the high-throughput screening of chemical activators and inhibitors for mammalian NAD biosynthesis. Another aspect of the invention provides a method of identifying a compound that effects in vivo activity of NAD metabolic enzymes. Further aspects of the invention include nucleic acid sequences, vectors, and transformed cells that can be used in the methods described herein.

1 Claim, 16 Drawing Sheets

OTHER PUBLICATIONS

Greengard, Pituitary Influence on Pyridine Nucleotide Metabolism of Rat Liver, 1964, J Biol Chem, 239/6, pp. 1887-1892.

Imai, "Transcriptional Silencing and Longevity Protein Sir2 is an NAD-Dependent Histone Deacetylase," 2000, Nature, 403, pp. 795-800.

Jacobson, "Evaluating the Role of Niacin in Human Carcinogenesis," 1995, Biochimie, 77, pp. 394-398.

Jacobson, "Mapping the Role of NAD Metabolism in Prevention and Treatment of Carcinogenesis," 1999, Mol Cell Biochem, 193, pp. 69-74.

Kaplan, "Pyridine Nucleotide Synthesis in the Mouse," 1956, J Biol Chem, 219, pp. 287-298.

Koubova, "How Does Calorie Restriction Work?" 2003, Genes Dev, 17, pp. 313-321.

Lin, "Nicotinamide Adenine Dinucleotide, a Metabolic Regulator of Transcription, Longevity and Disease," 2003, Curr Opin Cell Biol, 15, pp. 241-246.

Luo, "Negative Control of p53 by Sir2 alpha Promotes Cell Survival Under Stress," 2001, Cell, 107, pp. 137-148.

Mack, "Wallerian Degeneration of Injured Axons and Synapses is Delayed by a Ube4b/Nmnat Chimeric Gene," 2001, Nature Neuro, 4/12, 1199-1206.

Martin, "Identification of a Plasmid-Encoded Gene from *Haemophilus ducreyi* Which Confers NAD Independence," 2001, J Bact, 183/4, pp. 1168-1174.

Magni, "Enzymology of NAD+ Synthesis," 1999, Adv Enzymol Relat Areas Mol Biol, 73, pp. 135-182, xi, Abstract Only.

Micheli, "Determining NAD Synthesis in Erythrocytes," 1997, Methods Enzymol, 280, pp. 211-221.

Moazed, "Enzymatic Activities of SIR2 and Chromatin Silencing," 2001, Curr Opin Cell Biol, 13, pp. 232-238.

Motta, "Mammalian SIRT1 Represses Forkhead Transcription Factors," 2004, Cell, 116, pp. 551-563.

Moynihan, "Increased Dosage of Mammalian SIR2 in Pancreatic Beta Cells Enhances Glucose-Stimulated Insulin Secretion in Mice," 2005, Cell Metab, 2, pp. 105-117.

Picard, "SIRT1 Promotes Fat Mobilization in White Adipocytes by Repressing PPAR-y," 2004, Nature, 429, pp. 771-776.

Revollo, "The NAD Biosynthesis Pathway Mediated by Nicotinamide Phosphoribosyltransferase Regulates SIR2 Activity in Mammalian Cells*," 2004, J Biol Chem, 279/49, pp. 50754-50763.

Rongvaux, "Pre-B-Cell Colony-Enhancing Factor, Whose Expression is Up-Regulated in Activated Lymphosytes, Is a Nicotinamide Phosphoribosyltransferase, A Cytosolic Enzyme Involved in NAD Biosynthesis," 2002, Eur J Immunol, 32, pp. 3225-3234.

Rogvaux, "Reconstructing Eukaryotic NAD Metabolism," 2003, BioEssays, 25, pp. 683-690.

Samal, "Cloning and Characterization of the cDNA Encoding a Novel Human Pre-B-Cell Colony-Enhancing Factor," 1994, Mol Cell Biol, 14, pp. 1431-1437.

Schweiger, "Characterization of Recombinant Human Nicotinamide Mononucleotide Adenylyl Transferase (NMNAT), a Nuclear Enzyme Essential for NAD Synthesis," 2001, FEBS Letter, 492, pp. 95-100.

Vaziri, "hSIR2SIRT1 Functions as an NAD-Dependent p53 Deacetylase," 2001, Cell, 107, pp. 149-159.

Wood, "Sirtuin Activators Mimic Caloric Restriction and Delay Aging in Metazoans," 2004, Nature, 430, pp. 686-689.

\* cited by examiner

Yeast

Mammals

FIG. 7A

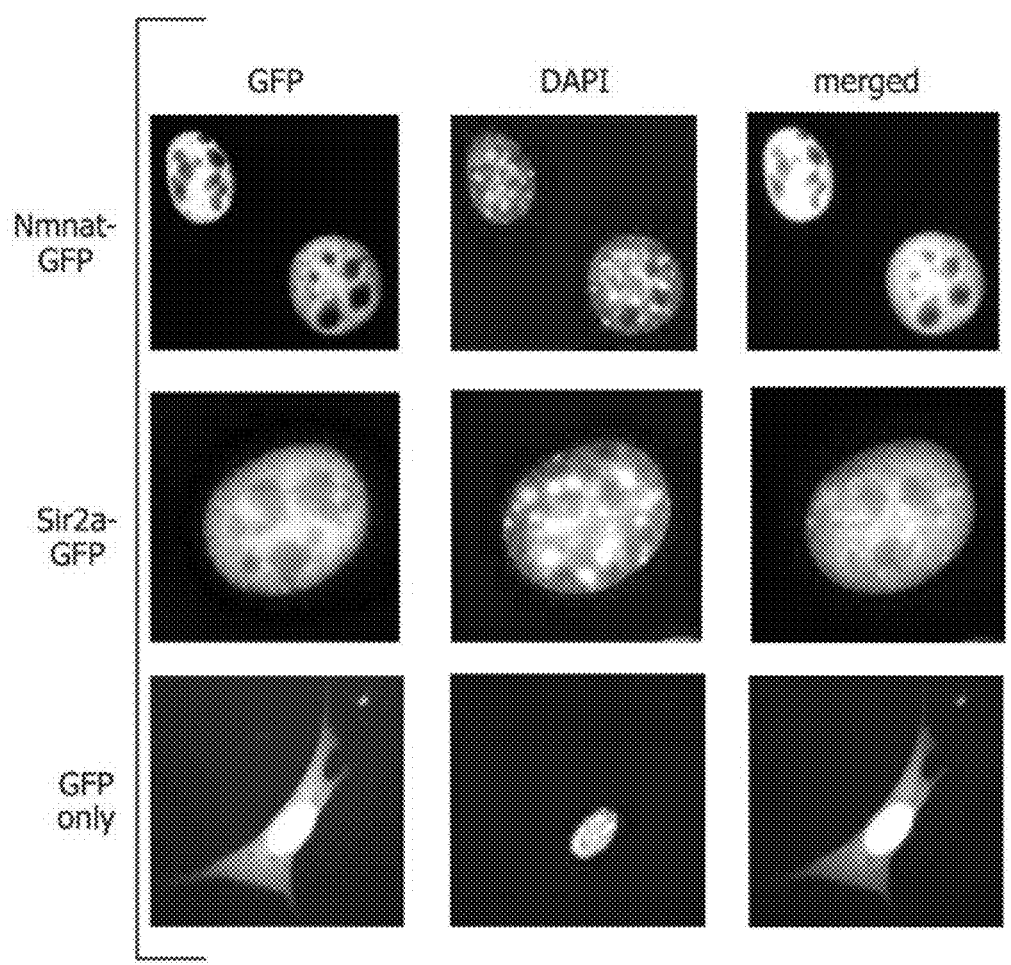

SEQUENCE LISTING

```
<160> NUMBER OF SEQ ID NOS: 4

<210> SEQ ID NO 1
<211> LENGTH: 1338
<212> TYPE: DNA
<213> ORGANISM: Artificial Sequence
<220> FEATURE:
<223> OTHER INFORMATION: GAL4DBD-mCORE nucleic acid sequence

<400> SEQUENCE: 1
atgaagctac tgtcttctat cgaacaagca tgcgatattt gccgacttaa aaagctcaag      60
tgctccaaag aaaaaccgaa gtgcgccaag tgtctgaaga caactgggga gtgtcgctac     120
tctcccaaaa ccaaaggtc tccgctgact agggcacatc tgacagaagt ggaatcaagg     180
ctagaaagac tggaacagct atttctactg attttcctc gagaagacct tgacatgatt     240
ttgaaaatgg attctttaca ggatataaaa gcattgttaa caggattatt tgtacaagat     300
aatgtgaata aagatgccgt cacagataga ttggcttcag tggagactga tatgcctcta     360
acattgagac agcatagaat aagtgcgaca tcatcatcgg aagagagtag taacaaaggt     420
```

```
caaagacagt tgactgtatc gccggaattc ctttcagaac caccaaagcg gaaaaaaga        480 aaagatatca atacaattga agatgctgtg aagttactgc aggagtgtaa aaagataata        540
gttctgactg gagctggggt ttctgtctcc tgtgggattc ctgacttcag atcaagagac        600
ggtatctatg ctcgccttgc ggtggacttc ccagacctcc cagaccctca agccatgttt        660
gatattgagt attttagaaa agacccaaga ccattcttca gtttgcaaa ggaaatatat         720 cccggacagt tccagccgtc tctgtgtcac aaattcatag ctttgtcaga taaggaagga       780
aaactacttc gaattatac tcaaaatata gataccttgg agcaggttgc aggaatccaa        840
aggatccttc agtgtcatgg ttcctttgca acagcatctt gcctgatttg taaatacaaa       900
gttgattgtg aagctgttcg tggagacatt tttaatcagg tagttcctcg gtgccctagg       960
tgcccagctg atgagccact tgccatcatg aagccagaga ttgtcttctt tggtgaaaac      1020
ttaccagaac agtttcatag agccatgaag tatgacaaag atgaagttga cctcctcatt      1080
gttattggat cttctctgaa agtgagacca gtagcactaa ttccaagttc tatacccat       1140 gaagtgcctc aaatattaat aaatagggaa cctttgcctc atctacattt tgatgtagag      1200
ctccttggag actgcgatgt tataattaat gagttgtgtc ataggctagg tggtgaatat     1260
gccaaacttt gttgtaaccc tgtaaagctt tcgaattccc ggggatccgt cgacgcgtct    1320
gcagaagctt ctagataa                                                   1338

<210> SEQ ID NO 2
<211> LENGTH: 450
<212> TYPE: DNA
<213> ORGANISM: Saccharomyces cerevisiae

<400> SEQUENCE: 2
atgaagctac tgtcttctat cgaacaagca tgcgatattt gccgacttaa aaagctcaag        60
tgctccaaag aaaaaccgaa gtgcgccaag tgtctgaaga caactgggaa gtgtcgctac       120
tctcccaaaa ccaaaaggtc tccgctgact agggcacatc tgacagaagt ggaatcaagg       180
ctagaaagac tggaacagct atttctactg attttcctc gagaagacct tgacatgatt        240
ttgaaaatgg attctttaca ggatataaaa gcattgttaa caggattatt tgtacaagat        300
aatgtgaata agatgccgt cacagataga ttggcttcag tggagactga tatgcctcta        360
acattgagac agcatagaat aagtgcgaca tcatcatcgg aagagagtag taacaaaggt       420
caaagacagt tgactgtatc gccggaattc                                         450

<210> SEQ ID NO 3
<211> LENGTH: 19
<212> TYPE: DNA
<213> ORGANISM: Saccharomyces cerevisiae

<400> SEQUENCE: 3
gaggacagta ctccgctcg                                                      19

<210> SEQ ID NO 4
<211> LENGTH: 445
<212> TYPE: PRT
<213> ORGANISM: Artificial Sequence
<220> FEATURE:
<223> OTHER INFORMATION: GAL4DBD-mCORE amino acid sequence

<400> SEQUENCE: 4

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
```

```
                    20                  25                  30
Lys Asn Asn Trp Glu Cys Arg Tyr Ser Pro Lys Thr Lys Arg Ser Pro
                35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Ser Glu Glu Ser Ser Asn Lys Gly Gln Arg Gln Leu
                130                 135                 140

Thr Val Ser Pro Glu Phe Leu Ser Glu Pro Pro Lys Arg Lys Lys Arg
145                 150                 155                 160

Lys Asp Ile Asn Thr Ile Glu Asp Ala Val Lys Leu Leu Gln Glu Cys
                165                 170                 175

Lys Lys Ile Ile Val Leu Thr Gly Ala Gly Val Ser Val Ser Cys Gly
                180                 185                 190

Ile Pro Asp Phe Arg Ser Arg Asp Gly Ile Tyr Ala Arg Leu Ala Val
                195                 200                 205

Asp Phe Pro Asp Leu Pro Asp Pro Gln Ala Met Phe Asp Ile Glu Tyr
                210                 215                 220

Phe Arg Lys Asp Pro Arg Pro Phe Phe Lys Phe Ala Lys Glu Ile Tyr
225                 230                 235                 240

Pro Gly Gln Phe Gln Pro Ser Leu Cys His Lys Phe Ile Ala Leu Ser
                245                 250                 255

Asp Lys Glu Gly Lys Leu Leu Arg Asn Tyr Thr Gln Asn Ile Asp Thr
                260                 265                 270

Leu Glu Gln Val Ala Gly Ile Gln Arg Ile Leu Gln Cys His Gly Ser
                275                 280                 285

Phe Ala Thr Ala Ser Cys Leu Ile Cys Lys Tyr Lys Val Asp Cys Glu
                290                 295                 300

Ala Val Arg Gly Asp Ile Phe Asn Gln Val Val Pro Arg Cys Pro Arg
305                 310                 315                 320

Cys Pro Ala Asp Glu Pro Leu Ala Ile Met Lys Pro Glu Ile Val Phe
                325                 330                 335

Phe Gly Glu Asn Leu Pro Glu Gln Phe His Arg Ala Met Lys Tyr Asp
                340                 345                 350

Lys Asp Glu Val Asp Leu Leu Ile Val Ile Gly Ser Ser Leu Lys Val
                355                 360                 365

Arg Pro Val Ala Leu Ile Pro Ser Ser Ile Pro His Glu Val Pro Gln
                370                 375                 380

Ile Leu Ile Asn Arg Glu Pro Leu Pro His Leu His Phe Asp Val Glu
385                 390                 395                 400

Leu Leu Gly Asp Cys Asp Val Ile Ile Asn Glu Leu Cys His Arg Leu
                405                 410                 415

Gly Gly Glu Tyr Ala Lys Leu Cys Cys Asn Pro Val Lys Leu Ser Asn
                420                 425                 430

Ser Arg Gly Ser Val Asp Ala Ser Glu Ala Ser Arg
                435                 440                 445
```

NAD BIOSYNTHESIS SYSTEMS

CROSS REFERENCE TO RELATED APPLICATIONS

This application is the national stage application of International Application Serial No. PCT/US2005/33611, filed Sep. 20, 2005, and claims the benefit of U.S. patent application Ser. No. 60/611,799, filed Sep. 20, 2004, and U.S. patent application Ser. No. 60/645,174, filed Jan. 20, 2005, the content of each of which is hereby incorporated herein by reference.

FIELD OF THE INVENTION

The present invention generally relates to a nicotinamide adenine dinucleotide (NAD) biosynthesis system and methods of screening for NAD biosynthesis effectors.

BACKGROUND

Nicotinamide adenine dinucleotide (NAD) plays fundamental roles in both cellular energy metabolism and cellular signaling. In energy metabolism, the chemistry of the pyridine ring allows NAD to readily accept and donate electrons in hydride transfer reactions catalyzed by numerous dehydrogenases. Recent studies have revealed new roles for nicotinamide adenine dinucleotide (NAD) and its derivatives in transcriptional regulation (Lin and Guarente, Curr. Opin. Cell. Biol., (2003) 15, 241-246). The evolutionarily conserved Sir2 protein family requires NAD for its deacetylase activity and regulates a variety of biological processes, such as stress response, differentiation, metabolism, and aging. Despite its absolute requirement for NAD, the regulation of Sir2 function by NAD biosynthesis pathways is poorly understood in mammals.

NAD biosynthesis in vertebrates is markedly different from that of yeast and invertebrates (see FIG. 1). For example, vertebrates lack any obvious homolog of the yeast nicotinamidase (Pnc1) (Rongvaux et al., Bioessays (2003) 25, 683-690). Also, nicotinamide, rather than nicotinic acid, is the major substrate for NAD biosynthesis in mammals (Magni et al., Adv. Enzymol. Relat. Areas Mol. Biol. (1999) 73, 135-182). NAD biosynthesis from nicotinamide (and nicotinic acid) is conserved throughout vertebrates, including mammals. Furthermore, the recycling of nicotinamide into NAD is more direct in vertebrates (see FIG. 1B).

Nicotinamide/nicotinic acid mononucleotide adenylyltransferase (Nmnat) catalyzes two reactions in NAD biosynthesis. Nmnat catalyzes the conversion of NaMN to deamido-NAD, which in turn is converted to NAD by NAD synthetase. In mammals, Nmnat also plays a role in the recycling of NAD. NAD is reformed via the Nampt and Nmnat enzymes, which convert nicotinamide to nicotinamide mononucleotide (NMN) and then NMN to NAD, respectively (Emanuelli et al., J. Biol. Chem. (2001) 276, 406-412; Schweigler et al., FEBS Lett. (2001) 492, 95-100). It has been reported that nicotinamide administration to mammals causes an increase in NAD levels in tissues such as liver and kidney (Kaplan et al., J. Biol. Chem. (1956) 219, 287-298; Greengard et al., J. Biol. Chem. (1964) 239, 1887-1892).

Co-factors for NAD biosynthesis include PRPP, ATP, and $MgCl_2$ (Magni et al., Adv. Enzymol. Relat. Areas Mol. Biol. (1999) 73, 135-182). PRPP is a substrate of Nampt and, along with nicotinamide, forms NMN. ATP is a co-substrate of Nmnat, donating adenine to synthesize NAD from NMN. In the Nmnat reaction, $MgCl_2$ is necessary for optimal Nmnat activity (Emanuelli et al., J. Biol. Chem. (2001) 276, 406-412).

Both the Nampt and Nmnat enzymes have been identified and cloned, but the kinetic characteristics of the NAD biosynthesis pathway mediated by Nampt and Nmnat have not been determined. The Nmnat enzyme has been described in mouse (Conforti et al., Proc. Natl. Acad. Sci. USA (2000) 97, 11377-11382; Mack et al., Nat. Neurosci. (2001) 4, 1199-1206) and humans (Schweigler et al., FEBS Lett. (2001) 492, 95-100; Emanuelli et al., J. Biol. Chem. (2001) 276, 406-412; Fernando et al., Gene (2002) 284, 23-29). The bacterial Nampt enzyme was originally identified in *Haemophilus ducreyi* (Martin et al., J. Bacteriol. (2001) 183, 1168-1174) and found highly homologous to the human pre-B-cell colony-enhancing factor (PBEF), a presumptive cytokine whose cDNA was originally cloned in 1994 (Samal et al., Mol. Cell. Biol. (1994) 14, 1431-1437). Nampt enzymatic activity was detected from the mouse PBEF protein, whose cDNA was cloned in 2002 (Rongvaux et al., Eur. J. Immunol. (2002) 32, 3225-3234).

In mammals, the enzyme Sir2 acts upon NAD substrate to form nicotinamide and O-acetyl-ADP-ribose (Imai et al., Nature (2000) 403, 795-800; Moazed, Curr. Opin. Cell. Biol. (2001) 13, 232-238; Denu, Trends Biochem. Sci. (2003) 28, 41-48). Even though the [NAD]/[NADH] ratio modulates Sir2 function in skeletal muscle differentiation in mammals (Fulco et al., Mol. Cell. (2003) 12, 51-6213), it is uncertain whether NAD biosynthesis regulates Sir2 activity in these organisms. It has been suggested that nicotinamide plays a critical role as an endogenous inhibitor of Sir2 in yeast (Anderson et al., Nature (2003) 423, 181-185; Gallo et al., Mol. Cell. Biol. (2004) 24, 1301-1312).

There have been a number of studies to measure NAD biosynthesis. For example, NAD biosynthesis in erythrocytes has been measured (Micheli et al., Methods Enzymol. (1997) 280, 211-221). A liquid chromatographic-electrospray ionization ion trap mass spectrometry (LC/MS) method has been developed to measure the biosynthetic incorporation of specific precursors into NAD (Evans et al., Anal. Biochem. (2002) 306, 197-203). In addition, the Nmnat enzymatic activity has also been quantitatively measured (Balducci et al., Anal. Biochem. (1995) 228, 64-68; Emanuelli et al., J. Chromotogr. B. (1996) 676, 13-18; Emanuelli et al., J. Biol. Chem. (2001) 276, 406-412). Revollo et al. (2004) J. Biol. Chem. 279(49): 50754-50763 (published online on Sep. 20, 2004, doi:10.1074/jbc.M408388200)) is reported to have determined the enzymological parameters of Nampt and Nmnat.

NAD has been linked to age-associated diseases (Lin and Guarente, Curr. Opin. Cell. Biol., (2003) 15, 241-246) and carcinogenesis (Jacobson et al., Biochimie, (1995) 77, 394-398; Jacobson et al., Mol. Cell. Biochem. (1999) 193, 69-74). Regarding the connection to aging and age-associated diseases, Sir2 proteins have been demonstrated to play a role in regulating aging and longevity in lower eukaryotes, such as yeast, worms and flies (Blander and Guarente, Annu. Rev. Biochem. (2004) 73, 417-435; Wood et al., Nature (2004) 430, 686-689). Sir2 proteins are also required for the lifespan-extending effects of caloric restriction (Koubova and Guarente, Genes. Dev. (2003) 17, 313-321; Picard et al., Nature (2004) 429, 771-776; Cohen et al., Science (2004) 305, 390-392; Wood et al., Nature (2004) 430, 686-689). In mammals, Sir2 plays a role in mobilizing fat from adipose tissue (Picard et al., Nature (2004) 429, 771-776), protecting axons from injuries and toxic damages (Araki et al., Science (2004) 305, 1010-1013), and regulating insulin secretion in pancreatic β cells (Moynihan et al. Cell Metab. (2005) 2, 105-117).

Sir2 is also known to have anti-apoptotic effects (Luo et al., Cell (2001) 107, 137-148; Vaziri et al., Cell (2001) 107, 149-159; Motta et al., Cell (2004) 116, 551-563; Brunet et al., Science (2004) 303, 2011-2015) by enhancing cellular resistance to damages and stresses. NAD biosynthesis plays an important role in regulating Sir2 activity and thereby controls aging, at least in yeast (Anderson et al., J. Biol. Chem. (2002) 277, 18881-18890; Anderson et al., Nature (2003) 423, 181-185; Gallo et al., Mol. Cell. Biol. (2004) 24, 1301-1312)). The work reported herein also shows that NAD biosynthesis mediated by Nampt regulates Sir2 activity in mammals (see Revollo et al. (2004) J. Biol. Chem. 279(49): 50754-50763. Furthermore, it has recently been suggested that increasing NAD biosynthesis enhances Sir2 activity in neurons and may increase the resistance to neurodegenerative diseases (Araki et al., Science (2004) 305, 1010-1013).

SUMMARY OF THE INVENTION

Among the various aspects of the present invention is the provision of compositions, kits, and solutions directed to an in vitro reconstituted mammalian NAD biosynthesis system; in vitro and in vivo methods for the high-throughput screening of chemical activators and inhibitors of mammalian NAD biosynthesis; and nucleic acids, vectors, and cultured cells. Provided herein are robust and quantitative approaches for examining NAD biosynthesis, effectors of NAD biosynthesis, and enzymatic activity regulated by the NAD biosynthetic pathway. Furthermore, these approaches are particularly well suited for mammalian systems.

Briefly, therefore, one aspect of the present invention is directed to a new composition of NAD biosynthesis enzymes to reconstitute the NAD biosynthesis pathway starting from nicotinamide (a form of vitamin B3). The composition generally includes a nicotinamide phosphoribosyltransferase polypeptide (Nampt) and a mammalian nicotinamide mononucleotide adenylyltransferase polypeptide (Nmnat). Thus the NAD biosynthesis pathway can be reconstituted in vitro with these isolated enzymes and their substrates in an appropriate buffer.

Another aspect of the invention is directed to a kit for the in vitro biosynthesis of NAD. This kit includes a Nampt polypeptide and a Nmnat polypeptide. Preferably, the Nmnat polypeptide is mammalian. Within the kit, Nampt and Nmnat are contained in the same or separate vessels.

Another aspect of the invention is directed to an aqueous solution for the in vitro biosynthesis of NAD. This solution contains Nampt at a concentration of about 0.01 μg/mL to about 100 μg/mL. This solution also contains Nmnat, preferably mammalian Nmnat, at a concentration of about 0.01 μg/mL to about 200 μg/mL.

Another aspect of the invention is directed to an in vitro method of identifying a compound that effects NAD biosynthesis. This method includes the step of combining a test compound and an NAD biosynthesis composition to form an assay mixture. Generally, the NAD biosynthesis mixture contains Nampt and Nmnat, but can also contain buffers, substrates or substrate analogs, and co-factors necessary or helpful for the biosynthesis of NAD. The method further includes the step of detecting or quantifying NAD or NADH in the assay mixture. Such an in vitro assay can be used to screen chemical activators and inhibitors for mammalian NAD biosynthesis. Chemical effectors for mammalian NAD biosynthesis can mediate a variety of anti-aging effects including anti-obesity, neuroprotective, and pancreatic β cell-protective effects as well as be effective to treat cancers.

A further aspect of the invention is directed to an isolated nucleic acid that includes the nucleotide sequence of SEQ ID NO: 1, or a degenerate variant of SEQ ID NO: 1. Yet other aspects of the invention are directed to isolated nucleic acid sequences that share homology to SEQ ID NO: 1. Still other aspects of the invention are directed to vectors and transformed cells containing these nucleic acids.

A still further aspect of the invention is directed to a reporter gene transcription assay system. This assay methodology can detect and/or quantify the enzymatic activity of Sir2α (an NAD-dependent histone/protein deacetylase in mammalian cells) as well as the effect of NAD biosynthesis on the mammalian Sirt1/Sir2α. As there are few known genes that precisely reflect Sir2 activity in mammalian cells, this system provides a qualitative and/or quantitative method to measure Sir2 activity in mammalian cells. The assay methodology can also measure cellular and/or nuclear levels of NAD. Further, the assay method can also be used as a functional readout to test the effects of potential chemical activators or inhibitors for mammalian NAD biosynthesis and/or Sir2 regulation or activity. This method includes the step of combining a test compound and transformed cells containing the GAL4 DNA binding domain fused to the Sir2α catalytic core domain (GAL4 DBD-mCORE), a reporter gene, and at least one GAL4 DNA binding site. The method also includes the step of detecting expressed reporter protein in the cells. Generally, the presence of expressed reporter protein is an indicator of Sir2 enzyme activity.

Other objects and features will be in part apparent and in part pointed out hereinafter.

BRIEF DESCRIPTION OF THE DRAWINGS

FIG. 1 contains a schematic representation of the NAD biosynthesis pathways from nicotinamide in yeast and mammals.

FIG. 2 contains a schematic representation of the NAD biosynthesis pathway from nicotinamide, the image of a gel showing purified recombinant Nampt and Nmnat, a line and scatter graph depicting NADH as a function of time, and a trace graph of high performance liquid chromatography elution.

FIG. 4 contains a representation of a western blot and a bar graph, each depicting Nampt's role as the rate-limiting component in the mammalian NAD biosynthesis pathway initiated from nicotinamide. The effects of overexpression of Nampt, Nmnat, Sir2, and addition of nicotinamide on total cellular NAD levels were assessed in mouse NIH3T3 cells.

FIG. 5 contains two bar graphs depicting transcriptional regulatory activity of a Sir2 core domain recruited onto a reporter gene as a function of the increased dosage of Nampt.

FIG. 6 is a schematic representation of a microarray experiment and also a scatter plot showing the correlation between expression profiles for Nampt and Sir2α, demonstrating induction of common gene expression changes in mouse fibroblasts from Nampt and Sir2α overexpression.

Figure 7A:
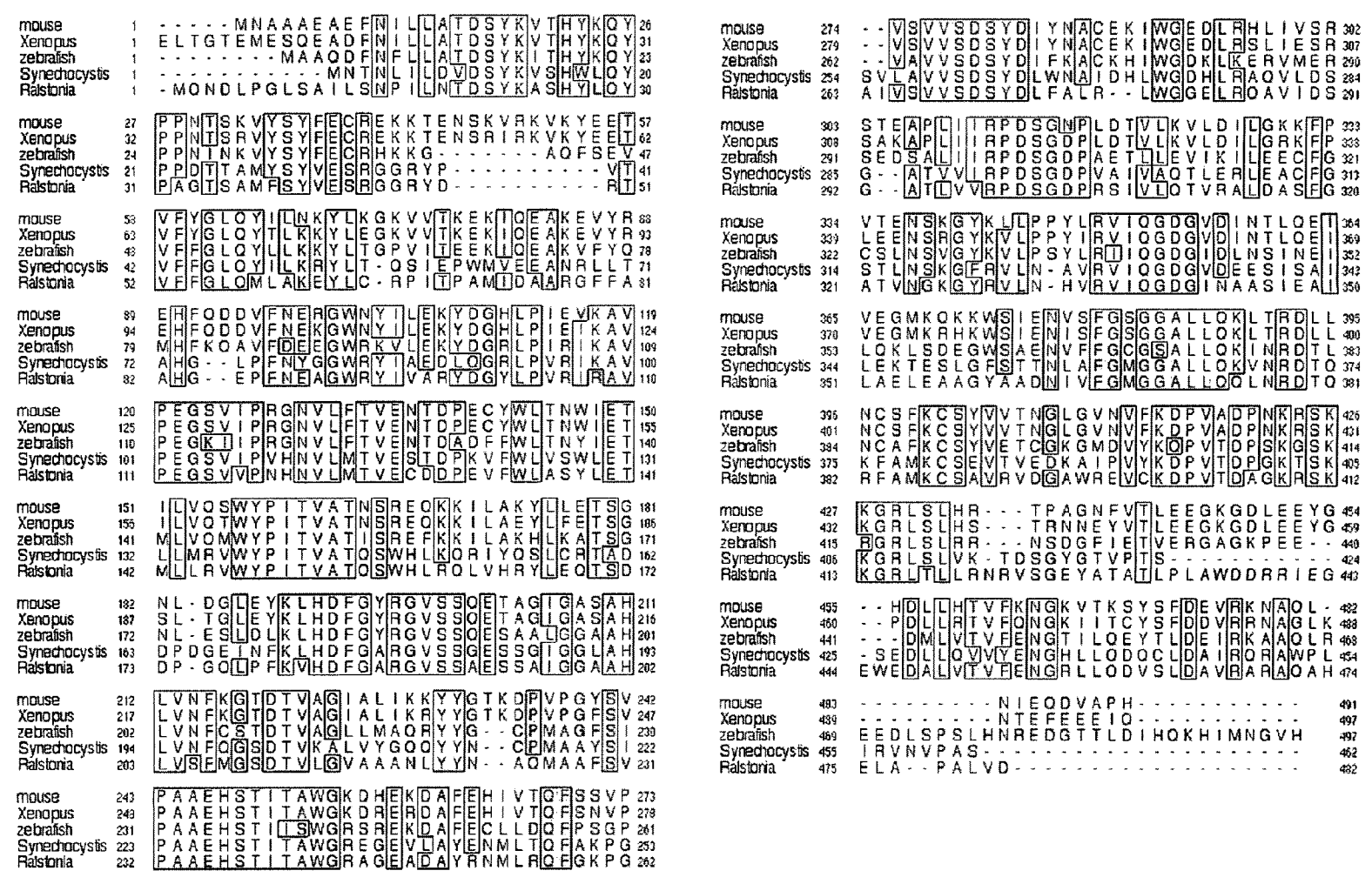

FIG. 7 lists comparative Nampt sequences and provides a phylogenetic tree of Nampt in several vertebrates and bacteria species. FIG. 7A is a comparison of amino acid sequences of Nampt in five representative species of vertebrates and bacteria. Identical amino acids are marked with shaded boxes. There is a very high sequence similarity ($P<10^{-103}$) among these Nampt polypeptides.

from nicotinamide and PRPP, it did not synthesize NaMN from nicotinic acid and PRPP.

Figure 9B:
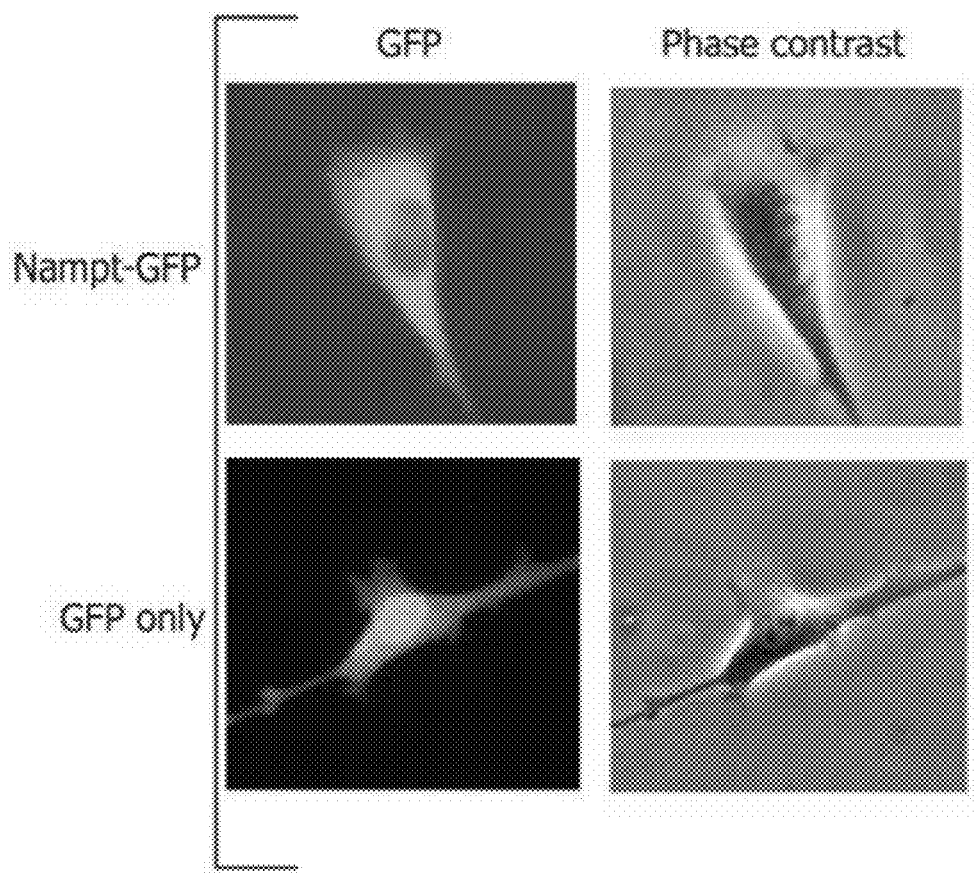

FIG. 9 is a series of images that depict fluorescent localization of GFP-fused Nampt, Nmnat and Sir2α. FIG. 9A shows establishment of NIH3T3 cell lines overexpressing Nmnat and Sir2α proteins fused to GFP at their Ctermini (Nmnat-GFP and Sir2α-GFP). An NIH3T3 cell line expressing GFP protein only was also established. The cells were fixed with 3.2% paraformaldehyde, treated with PBS containing 0.5% IGEPAL (Sigma), and stained with 50 ng/ml DAPI (see Example 3). Nmnat-GFP and Sir2α-GFP exhibited exclusive nuclear localization, as described in Luo et al., Cell (2001) 107, 137-148; and Schweigler et al., FEBS Lett. (2001) 492, 95-100 (see Example 3). FIG. 9B depicts transient expression in NIH3T3 cells of the Nampt polypeptide fused to GFP at its C-terminus (Nampt-GFP) and the control GFP protein. Live GFP-positive cells were examined and photographed under a fluorescent microscope. Nampt-GFP was mainly localized in cytoplasm, as described in Kitani et al., FEBS Lett. (2003) 544, 74-78.

ABBREVIATIONS AND DEFINITIONS

The term "amino acid" includes naturally occurring amino acids as well as non-naturally occurring amino acids, including amino acid analogs and derivatives. The latter includes molecules containing an amino acid moiety. One skilled in the art will recognize that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids. For all the amino acid sequences disclosed herein, it is understood that equivalent nucleotides and amino acids can be substituted into the sequences without affecting the function of the sequences. Such substitution is within the ability of a person of ordinary skill in the art.

As used herein, "polynucleotide" and "oligonucleotide" are used interchangeably and mean a polymer of at least two nucleotides joined together by phosphodiester bonds and may consist of either ribonucleotides or deoxyribonucleotides.

The term "polypeptide" when used herein refers to two or more amino acids that are linked by peptide bond(s), regardless of length, functionality, environment, or associated molecule(s). Typically, the polypeptide is at least four amino acid residues in length and can range up to a full-length protein. As used herein, "polypeptide," "peptide," and "protein" are used interchangeably.

As used herein, "sequence" means the linear order in which monomers occur in a polymer, for example, the order of amino acids in a polypeptide or the order of nucleotides in a polynucleotide.

Various embodiments of the present invention rely on altering biological material using molecular techniques. Molecular techniques refers to procedures in which DNA is manipulated in a test tube during at least one stage of the process, such as the direct manipulation of DNA or the use of shuttle host such as bacterium. Additional examples of molecular techniques include, for example, methods of using PCR to multiply a nucleic acid of interest for introduction and expression in a mammal or mammalian cell via expression vectors or direct introduction of the nucleic acid; methods of using nucleic acid libraries to determine, isolate, introduce, and express a nucleic acid of interest into a mammal or mammalian cell via expression vectors or direct introduction of the nucleic acid; isolation of nucleic acid segments, concatemerization of said nucleic acid segments into a larger nucleic acid, introduction, and expression of the same in a mammal or mammalian cell via expression vectors or direct introduction of the nucleic acid; and isolation of mRNA from a gene, creation of cDNA from the mRNA by reverse transcription, and introduction and expression of the same in a mammal or a cell via expression vectors or direct introduction of the nucleic acid. Such methods are well known in the art and are described in, for example, Sambrook et al. (2001), "Molecular Cloning, A Laboratory Manual," 3d ed., Cold Spring Harbor Laboratory Press.

DETAILED DESCRIPTION OF THE PREFERRED EMBODIMENTS

In accordance with the present invention, provided are in vitro-reconstituted mammalian NAD biosynthesis compositions, which can be used for the high-throughput screening of chemical activators and inhibitors for mammalian NAD biosynthesis, comprising two NAD biosynthesis enzymes. Also provided are kits and aqueous solutions useful for NAD biosynthesis. Further provided are in vitro and in vivo methods for identifying compounds that may effect NAD biosynthesis, along with nucleic acids, vectors, and cultured cells.

NAD Biosynthesis System

One aspect of the present invention is a composition that reconstitutes the NAD biosynthesis pathway starting from nicotinamide (a form of vitamin B3). Generally, the in-vitro NAD biosynthesis composition includes polypeptides of two major NAD biosynthesis enzymes, nicotinamide phosphoribosyltransferase (Nampt) and nicotinamide mononucleotide adenylyltransferase (Nmnat), which synthesize NAD from nicotinamide in mammals. The in-vitro NAD biosynthesis composition can also include various co-factors such as phosphoribosyl pyrophosphate (PRPP), ATP, magnesium ions (e.g., magnesium chloride) as well as substrates such as nicotinamide.

The Nampt and Nmnat polypeptides are, preferably, isolated polypeptides. That is, they are preferably separated from their natural or synthetic source. For example, if the isolated Nampt and/or Nmnat polypeptides are derived from their natural source, the isolated polypeptides have been removed or separated from their natural cellular environment and at least partially purified from other cellular nucleic acids, polypeptides, and other constituents. By way of further example, isolated Nampt and/or Nmnat polypeptides can be produced from, for example, linear synthesis, convergent synthesis, or solid-phase synthesis and removed from the synthesis mixture or at least partially purified or enriched. The isolated Nampt and/or Nmnat polypeptides can be in a cell-free solution or placed in a different cellular environment. Usually, the isolated Nampt and/or Nmnat polypeptide can constitute a significantly higher fraction (e.g., at least 2 fold, or more preferably at least 5 to 10 fold, or even more) of the total of amino acids present in the cells or solution of interest than in normal or diseased cells or in the cells from which the polypeptide was separated. A person skilled in the art can preferentially reduce the amount of other amino acid sequences present, or preferentially increase the amount of Nampt and/or Nmnat, or both. Generally, the isolated Nampt and/or Nmnat polypeptide will be relatively more pure than in a cellular environment. For example, the isolated Nampt and/or Nmnat polypeptides can be purified by at least one order of magnitude, preferably two or three orders, and more preferably four or five orders of magnitude. Similarly, isolated Nampt and/or Nmnat polypeptides can be preferably free of contamination, as indicated by purity levels of 90%, 95%, or 99%.

Nampt and Nmnat polypeptides can be isolated from tissues, cultured cells, or recombinant cell cultures by methods well-known in the art. Such cells include prokaryotic or eukaryotic cells. Preferably, Nmnat is a mammalian Nmnat. Nampt can be bacterial or mammalian Nampt. Methods of Nampt and Nmnat polypeptide isolation typically include lysing the recombinant cells and separating the polypeptide of interest from the rest of the cell polypeptides, nucleic acids, and fatty acid-based material using standard chromatography techniques known in the art. Such techniques include, but are not limited to, ammonium sulfate or ethanol precipitation, anion or cation exchange chromatography, phosphocellulose chromatography, hydrophobic interaction chromatography, affinity chromatography, hydroxylapatite chromatography, lectin chromatography, and high performance liquid chromatography (HPLC).

cDNAs encoding these enzymes can be isolated, for example, from a mammalian cDNA library (for example, a mouse liver cDNA library), the recombinant proteins expressed in a suitable host (for example an E. coli), and then purified (see e.g. Example 1). Thus the entire NAD biosynthesis pathway can be reconstituted in vitro with these recombinant enzymes and their substrates in an appropriate buffer. Appropriate buffers include HEPES and Tris.

To facilitate isolation, an amino acid tag can be added to the Nampt and/or Nmnat polypeptides using genetic engineering techniques that are well known to practitioners of the art. Preferably, Nampt and/or Nmnat include at least one, and more preferably six, consecutive histidine residues at either the amino or carboxy terminus of the protein. Such consecutive histidine residues are commonly referred to as a histidine tag. Terminal consecutive histidine residues can facilitate detection and/or purification of expressed recombinant proteins, and generally do not interfere with the function/activity/structure of the protein. The consecutive histidine residues can be incorporated into the protein coding gene by primers that carry the 5'-CAT-3' triplets. Consecutive histidine residues at either terminus serve as convenient aids for purification of proteins with immobilized metal affinity chromatography, which exploits the ability of the amino acid histidine to bind chelated transition metal ions such as nickel (Ni2+), zinc (Zn2+) and copper (Cu2+). Other techniques include, but are not limited to, epitopes for polyclonal or monoclonal antibodies including but not limited to the T7 epitope, the myc epitope, and the V5a epitope; and fusion of Nampt and Nmnat to suitable protein partners including but not limited to glutathione-S-transferase or maltose binding protein. These additional amino acid sequences can be added to the C-terminus of Nampt and Nmnat as well as the N-terminus or at intervening positions within the Nampt and Nmnat polypeptides.

Nampt and Nmnat can be present at a variety of concentrations. In one embodiment, Nampt is present in the composition at a concentration of about 0.01 µg/mL to about 100 g/mL. For example, the concentration of Nampt can be about 0.1 µg/mL to about 10 µg/mL or about 5 µg/mL. Preferably, Nmnat is present at a concentration about twice that of the concentration of Nampt. In one embodiment, Nmnat is present in the composition at a concentration of about 0.01 µg/mL to about 200 µg/mL. For example, the Nmnat concentration can be about 0.1 µg/mL to about 20 µg/mL, 1 µg/mL to about 10 µg/mL, or about 5 µg/mL. These concentrations of Nampt and/or Nmnat can occur in varying combinations and with either bacterial or mammalian polypeptides.

Co-factors for NAD biosynthesis can be included in the composition. Suitable co-factors include, but are not limited to, ATP, phosphoribosyl pyrophosphate (PRPP), and magnesium ions. In one embodiment, ATP is present in the composition at a concentration of about 0.01 mM to about 20 mM. As an example, ATP concentration can be about 0.1 mM to about 10 mM or about 0.5 mM to about 2 mM. In another embodiment, the co-factor PRPP is present at a concentration of about 0.1 µM to about 100 µM, for example, about 0.5 µM to about 10 µM, or about 1 µM to about 4 µM. In a further embodiment, the composition includes a magnesium ion. Preferably, the magnesium ion is a magnesium chloride. The composition can contain, for example, about 0.1 µM to about 100 µM, about 0.5 µM to about 10 µM, or about 1 µM to about 4 µM magnesium chloride. The composition can also contain, for example, about 0.1 mM to about 100 mM, about 1 mM to about 25 mM, or about 5 mM to about 15 mM magnesium chloride. Preferably, the composition contains about 12 mM of magnesium chloride. These various co-factors can be included as individual co-factors and in differing combinations with each other.

The composition can also include substrates for NAD biosynthesis. In one embodiment, nicotinamide, a substrate of Nampt, is present in the composition. In the Examples, biochemical analyses with enzyme-coupled fluorometric assays show that Nampt has a high affinity for nicotinamide (Km=0.92 mM) while the catalytic efficiency of Nampt is ~46-fold lower than that of Nmnat (see e.g. Example 2; Table 1).

TABLE 1

Kinetic parameters of purified recombinant mouse Nampt and Nmnat.

| Enzyme | Substrate | $K_m$ (µM) | $V_{max}$ (µmol/ min/mg) | Kcat (sec$^{-1}$) | Catalytic efficiency (kcat/$K_m$, M$^{-1}$ sec$^{-1}$) |
|---|---|---|---|---|---|
| Nampt | Nicotinamide | 0.92 | 0.021 | 0.020 | $2.17 \times 10^4$ |
| Nmnat | NMN | 20.1 | 34.1 | 20.0 | $9.95 \times 10^5$ |

The $K_m$ of Nampt is consistent with concentrations of nicotinamide in mammals, which have been reported at 0.4 to 0.5 µM in human serum (Bernofsky, Mol. Cell. Biochem. (1980) 33, 135-14348) and 0.34 µM in fasted human plasma (Jacobson, et al., Biochimie (1995) 77, 394-398). As explained above, NAD is reformed via the Nampt and Nmnat enzymes, which convert nicotinamide to nicotinamide mononucleotide (NMN) and then NMN to NAD, respectively. Nicotinamide is one of the two principal forms of the B-complex vitamin niacin. Nicotinamide, in addition to being known as niacinamide, is also known as 3-pyridinecarboxamide, pyridine-3-carboxamide, nicotinic acid amide, vitamin B3, and vitamin PP. Its molecular formula is $C_6H_6N_2O$ and its molecular weight is 122.13 daltons. Nicotinamide is commercially available from a variety of sources.

Substrate analogs can be included in the composition. In one embodiment, an analog of nicotinamide is present. Both nicotinamide and analogs of nicotinamide can both be in the composition. Analogs of nicotinamide include, for example, molecules that are: metabolized by Nmnat, inhibitors of Nmnat, metabolized by Nampt, inhibitors of Nampt, metabolized by Sir2, and/or inhibitors of Sir2. Examples of analogs that can be metabolized by Nmnat include, but are not limited to, nicotinamide mononucleotide (NMN), nicotinic acid mononucleotide (NaMN), nicotinamide adenine dinucleotide (NAD), nicotinic acid adenine dinucleotide (NaAD), ATP, inorganic pyrophosphate (PPi), tiazofurin, tazofurin adenine dinucleotide (TAD), selenazofurin, selenazofurin adenine dinucleotide, benzamide riboside monophosphate (BRMP), and benzamide riboside. Examples of analogs that can inhibit Nmnat include, but are not limited to, non-hydrolyzable TAD analogue beta-CH(2)-TAD; 1,3-bis(2-chloroethyl)-1-nitroso-urea (BCNU); nitrosobenzene; N-methyl-N'nitro-N-nitrosoguanidine (MNNG); and EDTA. Examples of analogs that can be metabolized by Nampt include, but are not limited to nicotinamide, phosphoribosyl pyrophosphate, nicotinamide mononucleotide (NMN), inorganic pyrophosphate (PPi), pyrazinamide, and pyrazinoic acid (POA). An example of an analog that can inhibit Nampt includes, but is not limited to, FK866. Examples of analogs that can be metabolized by Sir2 include, but are not limited to, nicotinamide adenine dinucleotide (NAD), acetyl-lysine, nicotinamide, and O-acetyl ADP-ribose. Examples of analogs that can inhibit Sir2 include, but are not limited to, nicotinamide, sirtinol, and splitomycin.

Substrates or substrate analogs can occur in the composition at a variety of concentrations. In one embodiment, nicotinamide and/or an analog of nicotinamide can be present in the composition at a concentration of about 0.1 µM to about 100 µM. For example, the concentration of nicotinamide and/or an analog of nicotinamide can be about 0.5 µM to about 10 µM, about 0.5 µM to about 8 µM, about 1 µM to about 4 µM, about 2 µM to about 3 µM, or about 2 µM. Nicotinamide and/or analogs of nicotinamide, in the concentrations discussed herein, can be used in conjunction with bacterial or mammalian Nampt, the various concentrations of Nampt discussed above, the various concentrations of Nmnat discussed above, and/or the various co-factors and co-factor concentrations discussed above.

The composition can also contain other components for determining the concentration of NAD or NADH. In one embodiment, the NAD biosynthesis composition further comprises an alcohol dehydrogenase enzyme along with ethanol. Using ethanol as a substrate, the alcohol dehydrogenase can convert NAD to NADH. Production of NADH provides the advantage of direct measure of NADH autofluorescence by way of a fluorometer. Both alcohol dehydrogenase and ethanol are commercially available from a variety of sources. In one embodiment, alcohol dehydrogenase is present in the NAD biosynthesis composition at a concentration of about 0.01 µg/mL to about 300 µg/mL. For example, the concentration of alcohol dehydrogenase can be about 0.1 µg/mL to about 30 µg/mL or about 1 µg/mL to about 5 µg/mL. Preferably, alcohol dehydrogenase is present in excess of the amount of Nampt. In one embodiment, ethanol is present in the NAD biosynthesis composition at a concentration of about 0.1% to about 5% of the volume of the mixture. For example, the ethanol concentration is about 1.5% of the volume. Alcohol dehydrogenase and ethanol, at the various concentrations discussed herein, can be used in conjunction with various embodiments of the invention that include bacterial or mammalian Nampt, the various concentrations of Nampt discussed above, the various concentrations of Nmnat discussed above, the various co-factors and co-factor concentrations discussed above, and/or nicotinamide or analogs of nicotinamide at the concentrations discussed above.

In another aspect of the invention, Nampt and mammalian Nmnat are packaged in the same or different vessels to form a kit for the in vitro biosynthesis of NAD. A compartmentalized kit includes any kit in which reagents are contained in the same or separate vessels. Examples of vessels include, but are not limited to, small glass containers, plastic containers, or strips of plastic or paper. These and other similar vessels allow the efficient transfer of reagents from one compartment to another compartment such that the samples and reagents are not cross-contaminated and the agents or solutions of each container can be added in a quantitative fashion from one compartment to another. Such containers can include a container which will accept the test sample, a container which contains the enzymes and/or polypeptides used in the assay, containers which contain NAD biosynthetic substrates and/or co-factors, containers which contain wash reagents (such as phosphate buffered saline, Tris-buffers, and—the like), and/or containers which contain reagents used to detect NAD or NADH, or the like. The kit can include sources and concentrations of Nampt and Nmnat as described above in the context of compositions of the invention. Also, the kit can include at least one co-factor necessary or helpful to the biosynthesis of NAD. Such co-factors, and concentrations of these co-factors, are as discussed above in the context of compositions of the invention. The kit can also include NAD biosynthesis substrates, such as nicotinamide or analogs of nicotinamide. Nicotinamide, analogs of nicotinamide, and concentrations thereof are as discussed previously. The kit can also include detection reagents. In a preferred embodiment, these detection reagents include alcohol dehydrogenase protein and ethanol. Concentrations of alcohol dehydrogenase protein and ethanol are as discussed previously in the context of compositions of the invention.

In still another aspect of the invention, Nampt and Nmnat are present in an aqueous solution for the in vitro biosynthesis of NAD. The Nampt and/or Nmnat can be freely solubilized in such a solution. Or, Nampt and/or Nmnat can be tethered to a solid substrate but solvated in the aqueous solution such that the enzymatic activities of the respective polypeptides are at least partially preserved. In one embodiment, this aqueous solution contains about 0.01 µg/mL to about 100 µg/mL of Nampt polypeptide and about 0.01 µg/mL to about 200 µg/mL of Nmnat polypeptide. For example, Nampt can be present in the aqueous solution at a concentration of about 0.1 µg/mL to about 10 µg/mL and preferably about 1 µg/mL to about 5 µg/mL. As another example, Nmnat can be present in the aqueous solution at a concentration of about 0.1 µg/mL to about 20 µg/mL, preferably, about 1 µg/mL to about 10 µg/mL, and more preferably about 5 µg/mL. In a preferred embodiment, Nmnat is present in the aqueous solution at a concentration about twice that of Nampt.

Sources of Nampt and Nmnat to be included in the various embodiments of the aqueous solution are as described above in the context of compositions of the invention. The aqueous solution can also include at least one co-factor necessary or helpful to the biosynthesis of NAD. Such co-factors, and concentrations of these co-factors, are as discussed above in the context of compositions of the invention. The aqueous solution can also include NAD biosynthesis substrates, such as nicotinamide or analogs of nicotinamide. Analogs of nicotinamide and concentrations of nicotinamide or analogs of nicotinamide are as discussed previously. The aqueous solution can also include detection reagents. Preferably, these detection reagents include alcohol dehydrogenase protein and ethanol. Concentrations of alcohol dehydrogenase protein and ethanol are as discussed previously in the context of compositions of the invention.

Effector Screen

Also provided is a method of identifying compounds that effect NAD biosynthesis. Such methods can be used for high-throughput chemical screening to find chemical activators and inhibitors for NAD biosynthesis enzymes. Generally, the method of identifying NAD biosynthesis effectors includes combining a test compound with an NAD biosynthesis composition to form an assay mixture and detecting or quantifying NAD and/or NADH formed in the assay mixture. The test compound can be, for example, a pyridine dinucleotide derivative. Detection of NAD and/or NADH can include, for example, a binary determination of whether or not any NAD and/or NADH is present. Quantification of NAD and/or NADH can include, for example, a determination of the relative amounts or concentration of NAD and/or NADH in the assay mixture. Quantifying NAD or NADH can be according to, for example, high performance liquid chromatography of NAD (see e.g. Example 3) or autofluorescence of NADH (see e.g. Example 2), respectively. NAD biosynthesis mixtures can include those in any of the NAD biosynthesis compositions, aqueous solutions, or kits described above.

Determining whether there exists a decrease or an increase in the concentration of NAD or NADH in the assay mixture can be included as a step in the method of identifying compounds that effect NAD biosynthesis. This decrease or increase in concentration can be, for example, in comparison to (i) the concentration of NAD and/or NADH in the NAD biosynthesis reaction and/or (ii) the concentration of NAD and/or NADH in the assay mixture at an earlier point in time. A decrease in the concentration of NAD or NADH is generally an indication that the test compound inhibits the synthesis of NAD. An increase in the concentration of NAD or NADH is generally an indication that the test compound activates the synthesis of NAD.

Alcohol dehydrogenase and ethanol can be present in the reaction mixture employed by the method of identifying compounds that effect NAD biosynthesis. Where alcohol dehydrogenase and ethanol are present, detection or quantification of NADH can include, for example, detecting the fluorescence of the assay mixture and then correlating this fluorescence to the concentration of NADH produced in the assay mixture. Detection of the autofluorescence of NADH can be performed with, for example, a commercially available fluorometer. Alcohol dehydrogenase and ethanol can be present in the various embodiments that include NAD detection, NADH detection, quantification of NAD, quantification of NADH, and determinations of increases or decreases of NAD, NADH, or both.

The reaction mixtures can be at a range of pH and temperature to function effectively within the method of identifying compounds that effect NAD biosynthesis. In one embodiment, the NAD biosynthesis mixture and/or the assay mixture has a pH of between about 6 to about 9. For example, the pH can be between about 7 to about 8. As another example, the pH can be about 7.5. In another embodiment, the NAD biosynthesis composition and/or the assay mixture has a temperature of between about 25° to about 40° C. For example, the temperature can be between about 30° to about 38° C. As another example, the temperature can be about 35° to about 37° C. As a further example, the temperature can be about 37° C. These various pHs and temperature levels can occur in various combinations as well as in conjunction with embodiments employing, among other elements and in various combinations and iterations, NAD detection, NADH detection, determination of NAD concentration, determination of NADH concentration, and determinations of increases or decreases of NAD, NADH, or both, alcohol dehydrogenase and ethanol, fluorometric detection, and HPLC detection, each of which are discussed above.

Nucleic Acids

Also provided is an isolated nucleic acid, wherein one embodiment has a nucleotide sequence of SEQ ID NO: 1. This sequence represents a GAL4 DNA binding domain fused to the Sir2α catalytic core domain (GAL4 DBD-mCORE). This fusion sequence can be a transcription repressor (see e.g. FIG. 5A). Further, Examples demonstrate that NAD-dependent deacetylase activity is correlated with this repressive activity (see e.g. Example 4). This sequence can also be used to measure the activity of Sir2 (see e.g. Example 4). The GAL4 DBD-mCORE effector can be transfected into cells and used to produce cell lines and/or transgenic mice in which these genes are integrated into their genomes.

In another embodiment, the isolated nucleic acid has a nucleotide sequence with at least 65% homology to SEQ ID NO: 1. As used herein, "percent homology" of two amino acid sequences or of two nucleic acids is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into NBLAST and XBLAST programs of Altschul et al. (J. Mol. Biol. 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g. XBLAST and NBLAST) are used. See BLAST: Basic Local Alignment Search Tool [online], [retrieved on 2004-09-20]. Retrieved from the Internet <URL: http://www.ncbi.nlm.nih.gov>. For example, the isolated nucleic acid can have at least 75% homology to SEQ ID NO: 1. In another example, the isolated nucleic acid has at least 85% homology to SEQ ID NO: 1. In a further example, the isolated nucleic acid has at least 95% homology to SEQ ID NO: 1.

Vectors

An expression vector is generally a replicable DNA construct used to express DNA which encodes the desired protein and which includes a transcriptional unit. The expression vector described herein is an expression vector that contains an isolated nucleic acid encoding GAL4 DBD-mCORE, as described above, operably linked to an expression control sequence. The transcriptional unit can comprise an assembly of (1) genetic element(s) having a regulatory role in gene expression, for example, promoters, operators, or enhancers, operatively linked to (2) a DNA sequence encoding a desired protein (in this case, a protein of the present invention) which is transcribed into mRNA and translated into protein, and (3) appropriate transcription and translation initiation and termination sequences. The choice of promoter and other regulatory elements generally varies according to the intended host cell. In the expression vectors, regulatory elements controlling transcription or translation can be generally derived from mammalian, microbial, viral, or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the term is intended to include such other forms of expression vectors which serve equivalent functions and which become known in the art subsequently hereto. A wide variety of vectors, into which nucleic acids of the invention can be inserted, are readily available from commercial sources. Examples include pSPORT vectors, pGEM vectors (Promega), pPROEX vectors (LTI, Bethesda, Md.), Bluescript vectors (Stratagene), pET vectors (Novagen) and pQE vectors (Qiagen).

Cultured Cell

Cultured cells can be transformed with the nucleic acids and/or vectors described above. Progeny of such transformed cells are also included in various embodiments. In general, the host cell may comprise any cellular organism including a prokaryotic cell or eukaryotic cell that is capable of being transformed with a vector comprising the isolated nucleic acids described above. The techniques of transforming and transfecting cells are well known in the art and may be found in such general references as Sambrook and Russel, Molecular Cloning: A laboratory Manual, 3d Ed. (2001) Cold Spring Harbor Laboratory Press, NY.

The vectors described above can be transformed into and expressed in many host cells. Transformed host cells may be cultured in conventional nutrient media modified as appropriate for inducing promoters, selecting transformants, or amplifying genes. The culture conditions, such as temperature, pH, and the like, will be apparent to the ordinarily skilled artisan.

The cultured cell can be transformed with an expression vector encoding GAL4 DBD-mCORE. The expression vector is as described above. Examples of cell culture and transformation are provided in Examples 1, 3, 4, and 5.

The cultured cell can contain an isolated nucleic acid described above. The cultured cell can also contain a reporter gene linked to at least one GAL4 DNA binding sequence. Preferably, the reporter gene is linked to about four GAL4 DNA binding sequences. An example of a suitable reporter gene is a luminescent reporter gene, such as a luciferase. In one embodiment, the reporter gene is encoded by SEQ ID NO: 3 or a degenerate variant of SEQ ID NO: 3, and linked to an expression control sequence.

SIR2 Transcription Assay

The effect of NAD biosynthesis on the Sir2 NAD-dependent deacetylase in mammalian cells can be detected and/or quantified with an assay methodology using a reporter gene transcription assay system. Nampt constitutes the rate-limiting step in NAD biosynthesis from nicotinamide, which is the main pathway to synthesize NAD in mammals (see e.g. Example 2). As demonstrated in the Examples, overexpression of Nampt significantly increased total cellular NAD in mouse fibroblasts, while increased dosage of Nmnat and addition of 5 mM nicotinamide were unable to increase NAD (see e.g. FIG. 4B). This pathway also regulates the transcriptional regulatory function of mammalian Sirt1/Sir2α, an NAD-dependent histone/protein deacetylase (see e.g. Example 3-4). Examples demonstrate that overexpression of Nampt enhanced the transcriptional repressive activity of the GAL4 DBD-fused Sir2α core domain (GAL4 DBD-mCORE) recruited onto a reporter gene (see e.g. FIG. 5B), consistent with their effects on total cellular NAD levels. The correlation between cellular NAD levels and repression of Sir2 is shown, for example, in FIG. 5D. So, overexpression of Nampt significantly increases total cellular NAD, which in turn represses the transcription activity of Sir2.

Because there are few known genes that precisely reflect Sir2 activity in mammalian cells, the GAL4 DBD-mCORE system can provide a quantitative and/or qualitative method to measure Sir2 activity in mammalian cells. This system can be used to measure cellular (or nuclear) levels of NAD by correlating the fold repression measured in this system with cellular NAD levels (see e.g. FIG. 5D). The system can also be used as a functional readout to test the effects of chemical activators and inhibitors for mammalian NAD biosynthesis. The GAL4 DBD-mCORE system can be used where the effector and reporter genes are co-transfected into cells. GAL4 DBD-mCORE can also be integrated into the genomes of cell lines/transgenic mice.

The method of identifying a compound that effects in vivo activity of NAD metabolic enzymes generally includes the steps of (i) combining a test compound and the cultured cell, or population of such cultured cells, described above and (ii) detecting or quantifying expressed reporter protein in the cell(s). Expressed reporter protein in the cell is generally the result of expression of the GAL4 DBD-mCORE sequence followed by recruitment of the expression product to a reporter containing a reporter gene and GAL4 binding sites. Detecting expressed reporter protein can include a binary determination of whether or not any expressed reporter protein is present. Quantification can be of the level or the activity of the expressed reporter protein. The level of expressed reporter protein can be quantified, for example, by chromatographic, immunologic, or spectral methods commonly understood in the arts. Activity measurement is illustrated, for example, in Example 4. The measured level or activity of expressed reporter protein can generally be considered an indicator of Sir2 enzyme activity.

Determining whether there exists a decrease or an increase in the concentration of NAD or NADH in the cell(s) of the in vivo assay can be a step in the method of identifying compounds that effect NAD biosynthesis. Generally, a decrease in the concentration of NAD is an indication that the test compound inhibits synthesis of NAD, while an increase in the concentration of NAD is an indication that the test compound activates synthesis of NAD. Thus, practice of various embodiments can provide a functional readout to test the effects of potential chemical inhibitors for mammalian NAD biosynthesis.

Preferably, the GAL4 DBD-mCORE expression product is recruited to a luciferase reporter that has a thymidine kinase minimal promoter and four GAL4 binding sites. A reporter gene can be any gene that is well characterized both genetically and biochemically, may be fused to regulatory regions of other genes, and whose activity is normally not detectable in the target organism into which it is transferred. Reporter gene activity is generally detectable by simple assays. One example of a reporter gene is a luminescent reporter gene. A luminescent reporter protein provides the advantage of detecting autofluorescence of expressed luminescent protein. An assay based upon fluorescence detection is both easy to perform and highly sensitive. Such genes encode luminescent proteins, which include, for example, aeqorin, β-galactosidase, β-glucoronidase, green fluorescent protein and its variants, bacterial luciferase, firefly luciferase, *Renilla* luciferase, *Vargula* luciferase, and secreted alkaline phosphatase. A preferred luminescent reporter gene encodes luciferase (luciferin; oxygen-4-oxidoreductase, EC 1.13.12.7).

Cultured cells are as described above. Preferably, the cultured cells contain both the GAL4 DBD-mCORE gene and a luciferase reporter gene linked to four, or about four, GAL4 DNA binding sequences.

Two populations of cells can be used in the method of identifying a compound that effects in vivo activity of NAD metabolic enzymes. Generally, the first and the second population of cells are of the same or similar type. The first population of cells is not exposed to the test compound. The second population of cells is exposed to the test compound. The expressed reporter protein presence, level, or activity is determined for both the first and the second population of cells. Then, the presence, level, or activity of reporter protein in the first population of cells is compared to that of the second population of cells.

Similarly, a third population of cells can also be employed in the assay. The cells of this third population generally comprise GAL4 DBD, but not the mCORE sequence. For example, the third population of cells can comprise a nucleic acid with a nucleotide sequence of SEQ ID NO: 2 along with either (a) a reporter gene linked to at least one GAL4 DNA binding sequence or (b) a reporter gene linked to a nucleic acid comprising a nucleotide sequence of SEQ ID NO: 3 or a degenerate variant of SEQ ID NO: 3. The sequence of SEQ ID NO: 2 encodes GAL4 DBD, but does not include the mCORE sequence. The sequence of SEQ ID NO: 3 encodes a GAL4 DNA binding site. This third population of cells can serve as, for example, a control, where the absence of the mCORE sequence, representing the Sir2 catalytic domain, provides a baseline activity which can be used to compare relative transcription of repression as possessed by, for example, cell lines containing the GAL4 DBD-mCORE sequence (see e.g. FIG. 5A). A line of cells with the GAL4 DBD sequence allows expressing the level or activity of reporter protein present in populations of cells containing GAL4 DBD-mCORE as a percentage of level or activity, respectively, of reporter protein present in the GAL4 DBD (i.e., baseline) population of cells. For example, the activity of reporter protein in GAL4 DBD-mCORE containing cells, those exposed to a test compound and those not exposed, can be expressed as a percentage of the activity of reporter protein in GAL4 DBD containing cells. Examples demonstrate the use of one, two, or three populations of cells in the methods of assaying activity of NAD metabolic enzymes (see e.g. Examples 3, 4, and 5).

The in vivo assay methodology can also include the step of correlating the level or activity of expressed reporter protein with a concentration of cellular NAD. A correlation in biology is the extent to which two statistical variables vary together or the interdependence between two variables (see e.g. Dictionary of Biochemistry and Molecular Biology, 2d. ed. John Wiley & Sons, 1989). The determination of relationships in biological assays by means of correlation is well known to those skilled in the art. Examples demonstrate a correlation between total cellular NAD levels and the transcriptional activities of GAL4 DBD-mCORE in control and stable Nampt-overexpressing NIH3T3 cell lines (see e.g. Example 5; FIG. 5D).

Figure 6A:
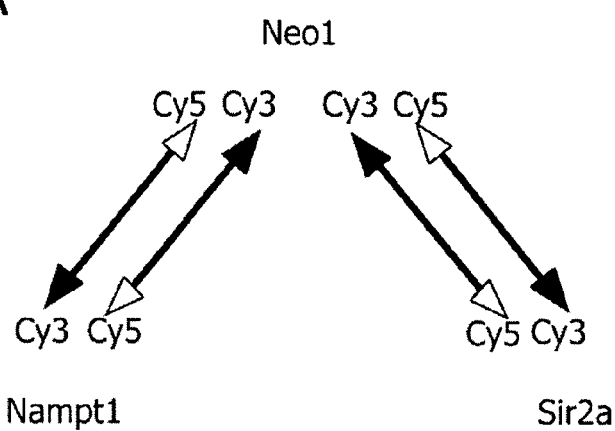
FIG. 6A depicts a scheme of microarray experiments. Four microarray hybridizations with dye-swaps were conducted for each pairwise comparison using biologically duplicated samples (see Example 5).
Figure 6B:
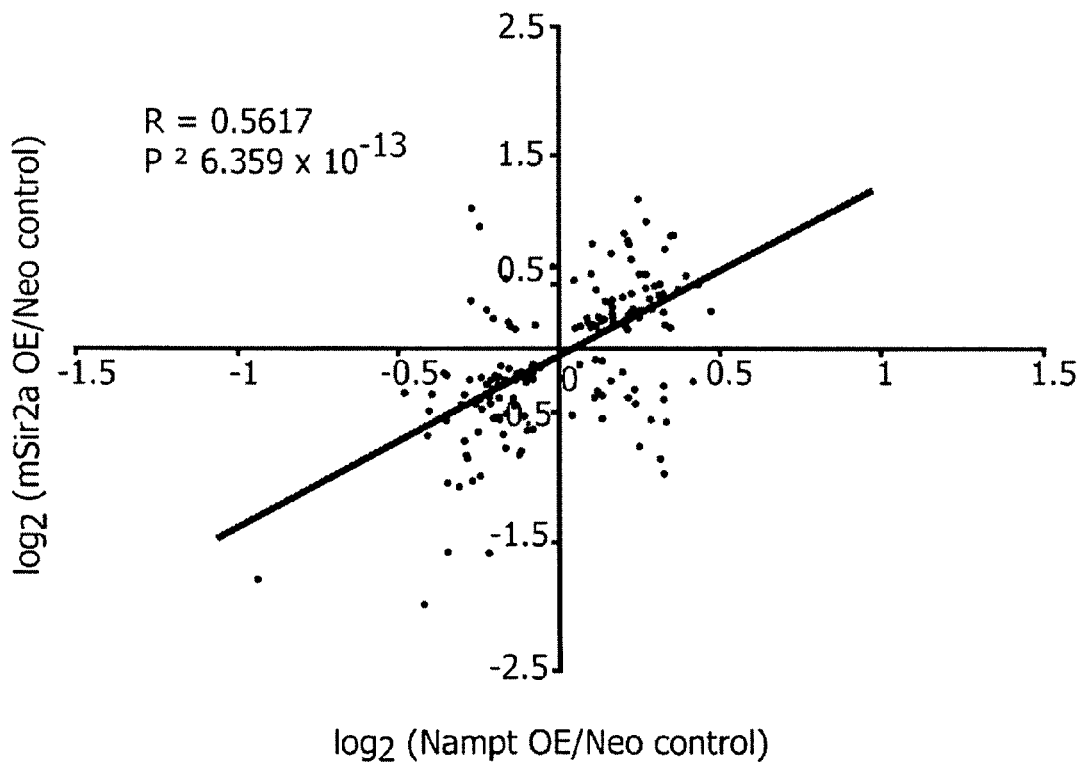
FIG. 6B depicts a scatter plot and regression analysis of expression profiles for Nampt and Sir2α. The gene expression profiles of Nampt- and Sir2α-overexpressing cells are significantly correlated (see Example 5). All genes changed with 95% confidence in both Nampt- and Sir2α-overexpressing cell lines are plotted. Statistical analysis of the correlation was determined by the Spearman non-parametric test.
Figure 6C:
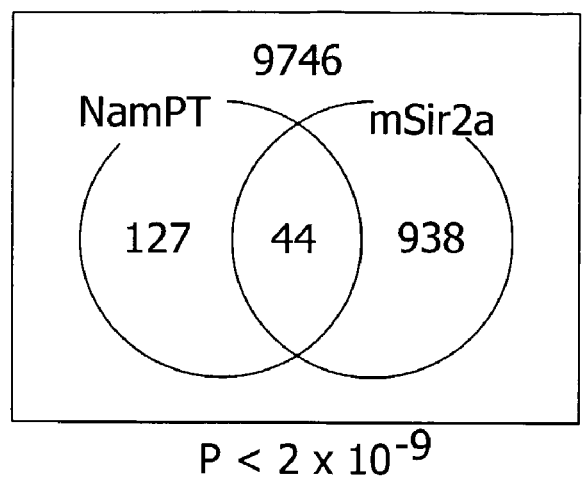
FIG. 6C depicts a Venn diagram for genes exhibiting ≧1.2-fold expression changes with 95% confidence in Nampt- and Sir2α-overexpressing cell lines (see Example 5). Statistical significance was determined by the hyper-geometric distribution test.
Figure 6D:
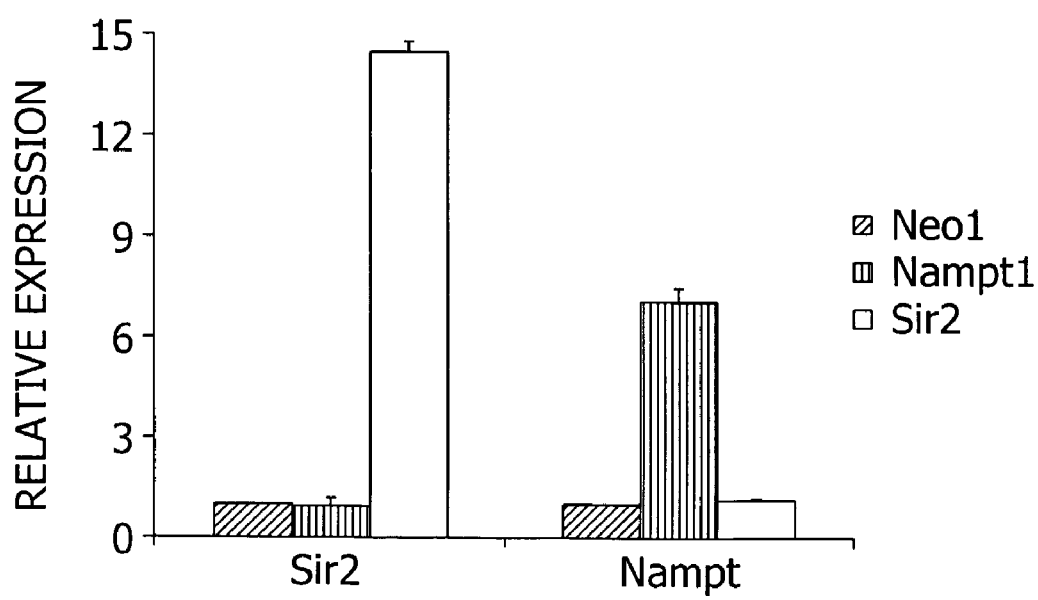
FIG. 6D is a bar graph depicting measurements of relative transcript levels of selected genes in Nampt- and Sir2α-overexpressing cell lines. The transcript levels were measured relative to the GAPDH gene and normalized to the Neo1 control. Averages and standard deviations were calculated from three independent RNA samples for each gene. Sir2α and Nampt were examined.
Figure 6E:
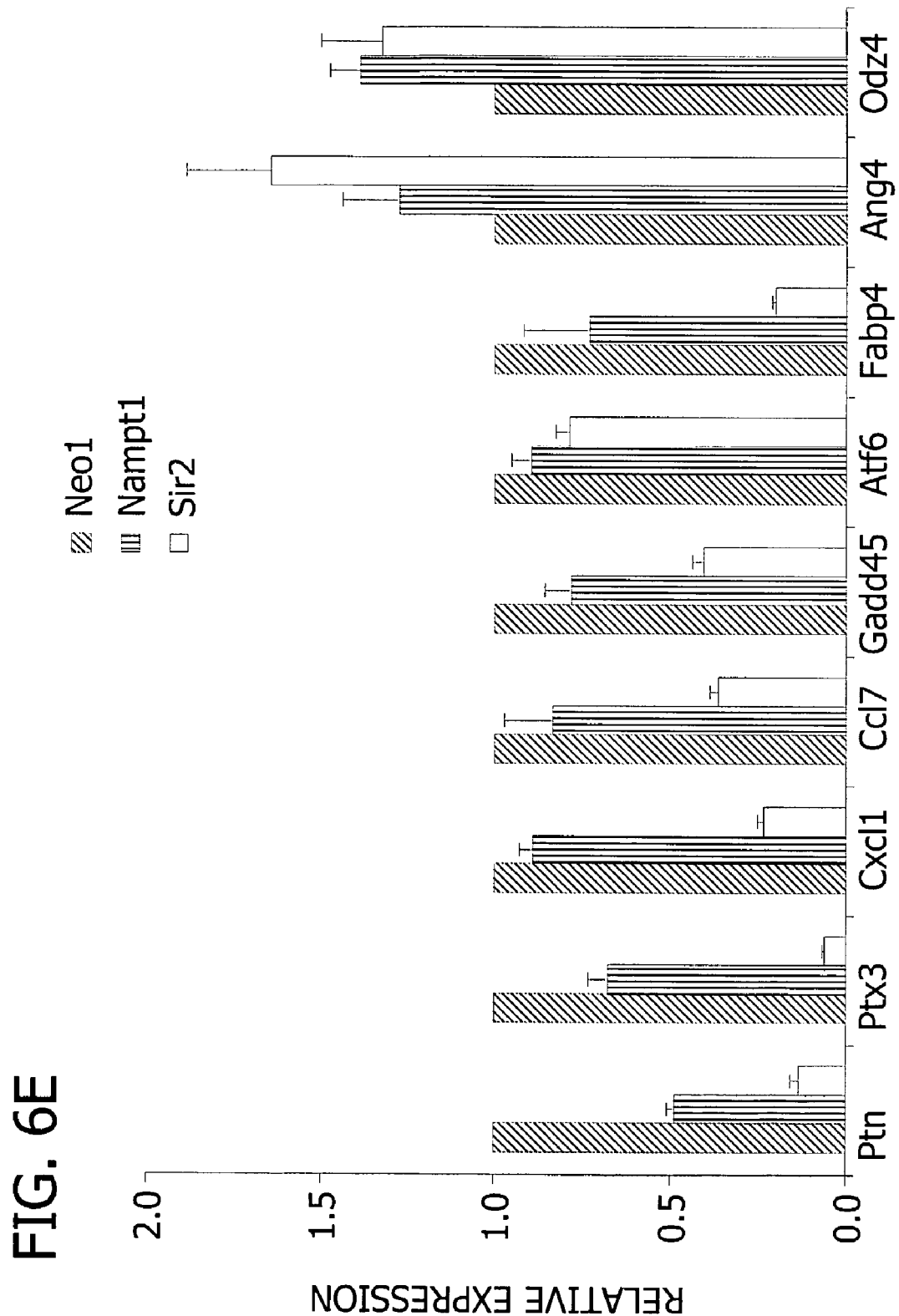
FIG. 6E is similar to FIG. 6D but with six down-regulated and two up-regulated genes examined. Ptn, pleiotrophin; Ptx3, pentaxin related gene 3; Cxcl1, chemokine (C-X-C morif) ligand 1; Ccl7, chemokine (C-C) motif ligand 7; Gadd45, growth arrest and DNA-damage-inducible 45; Aff6, activating transcription factor 6; Angpl4, angiopoietin-like 4; Odz4, odd OZ/ten-m homolog 4 (see Example 5). Fabp4 (fatty acid binding protein 4), which did not meet the criterion of 95% confidence in Nampt1, was also examined since it is a known target for Sir2 (Picard et al., Nature (2004) 429, 771-776).
Figure 7B:
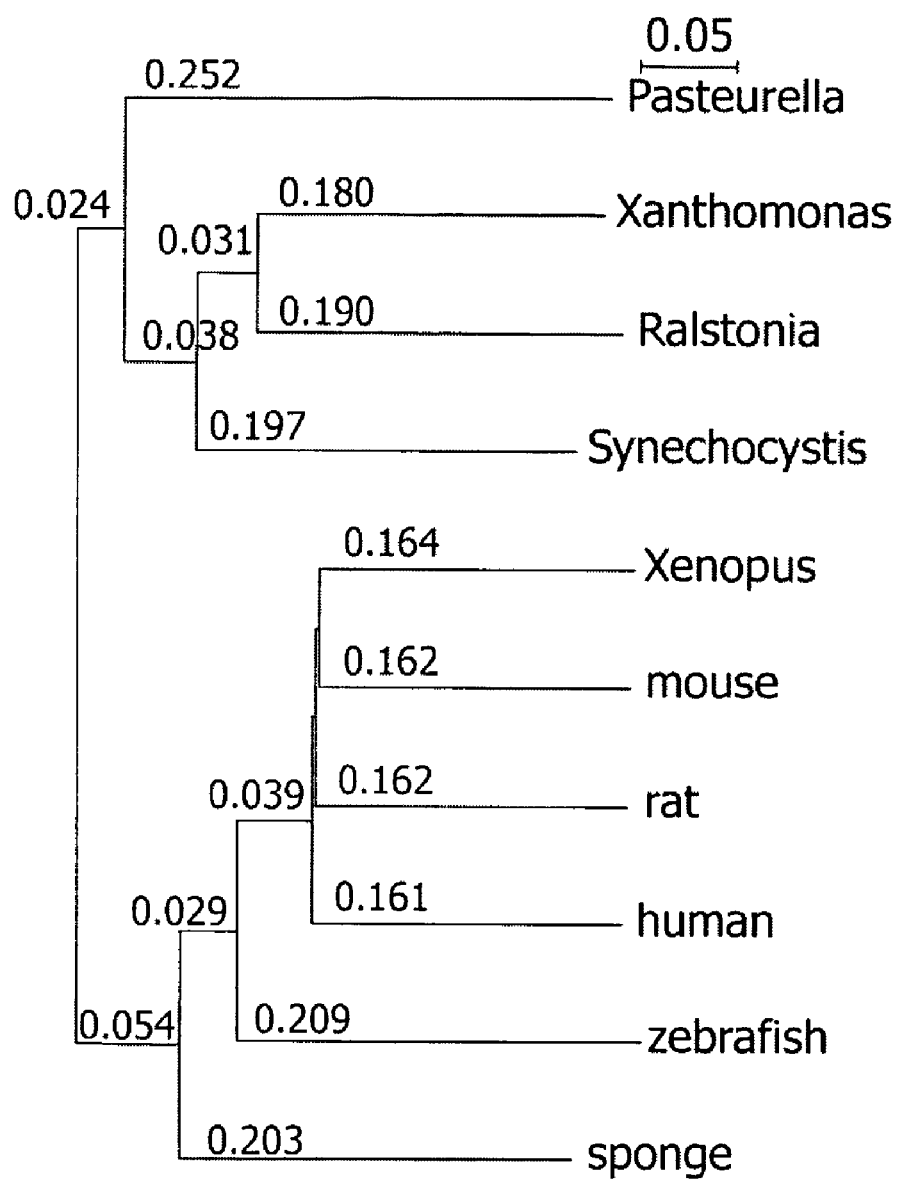
FIG. 7B depicts a phylogenetic tree of Nampt polypeptides in ten diverged species. Numbers show observed phylogenetic distances between nodes. Accession numbers referred to are: AE006139 for *Pasteurella multocida*, AE012463 for *Xanthomonas campestris*, AL646081 for Ralstonia solanacearum, D64005 for *Synechosystis* sp., Y18901 for sponge, BC045090 for *Xenopus*, BC044476 for zebrafish, AY679720 for mouse, AB081730 for rat, and U02020 for human.

The assay methodology can further include the step of correlating the decrease or the increase in the concentration of NAD with inhibition or activation, respectively, of enzymes involved in NAD biosynthesis. These enzymes, for example, include Nampt and/or Nmnat. As discussed above, the determination of relationships in biological assays by means of correlation is well known to those skilled in the art. Examples using gene expression profiling with oligonucleotide microarrays showed a significant correlation between expression changes in Nampt- and Sir2α-overexpressing cell lines (see e.g. Example 5; FIG. 6B). This correlation was confirmed by measuring transcript levels of representative genes with quantitative real-time RT-PCR (see e.g. Example 5; FIG. 6D-E).

There exists a range of the number of cells in each population that can be used in the in vivo assay. Generally, the population of cells can contain about $1\times10^4$ to $1\times10^6$ cells. For example, the population of cells can contain about $1\times10^5$ cells. Examples demonstrate various population sizes of cells used in procedures useful to the invention (see e.g. Examples 3 and 4). These numbers of cells can be useful in conjunction with various combinations and iterations of other elements such as detection means, measuring means, determinations of decrease or increase of NAD, comparisons of various populations of cells, correlation of detected and/or measured reporter protein to Sir2 activity, correlation of detected and/or measured reporter protein to cellular NAD levels, and various types of reporter proteins such as luminescent reporter proteins, each of which are discussed above.

A range of test compound concentrations can function within the in vivo assay methodology. In one embodiment, the test compound is present at a concentration of about 0.001 µM to about 10,000 µM. For example, the test compound can be present at a concentration of about 0.01 µM to about 1,000 µM. As another example, the test compound can be present at a concentration of about 0.1 µM to about 100 µM. As a further example, the test compound can be present at a concentration of about 1 µM to about 10 µM. These concentrations of test compound can be useful in conjunction with various combinations and iterations of other elements such as detection means, measuring means, determinations of decrease or increase of NAD, comparisons of various populations of cells, correlation of detected and/or measured reporter protein to Sir2 activity, correlation of detected and/or measured reporter protein to cellular NAD levels, various types of reporter proteins such as luminescent reporter proteins, and numbers of cells, each of which are discussed above.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Production of Recombinant Proteins

Figure 1A:
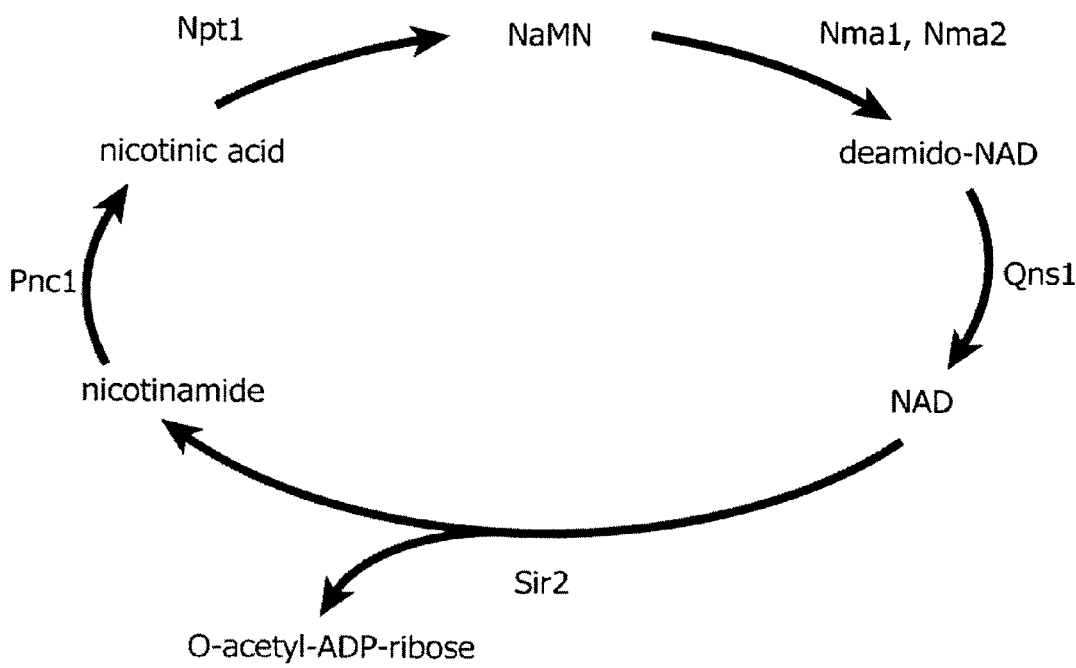
FIG. 1A shows NAD biosynthesis from nicotinamide in *Saccharomyces cerevisiae*. Pnc1, Npt1, Nma1 and Nma2, and Qns1 are nicotinamidase, nicotinic acid phosphoribosyltransferase, nicotinic acid mononucleotide adenylyltransferase 1 and 2, and NAD synthetase, respectively. This pathway is also conserved in *C. elegans, Drosophila* and other invertebrates.
Figure 1B:
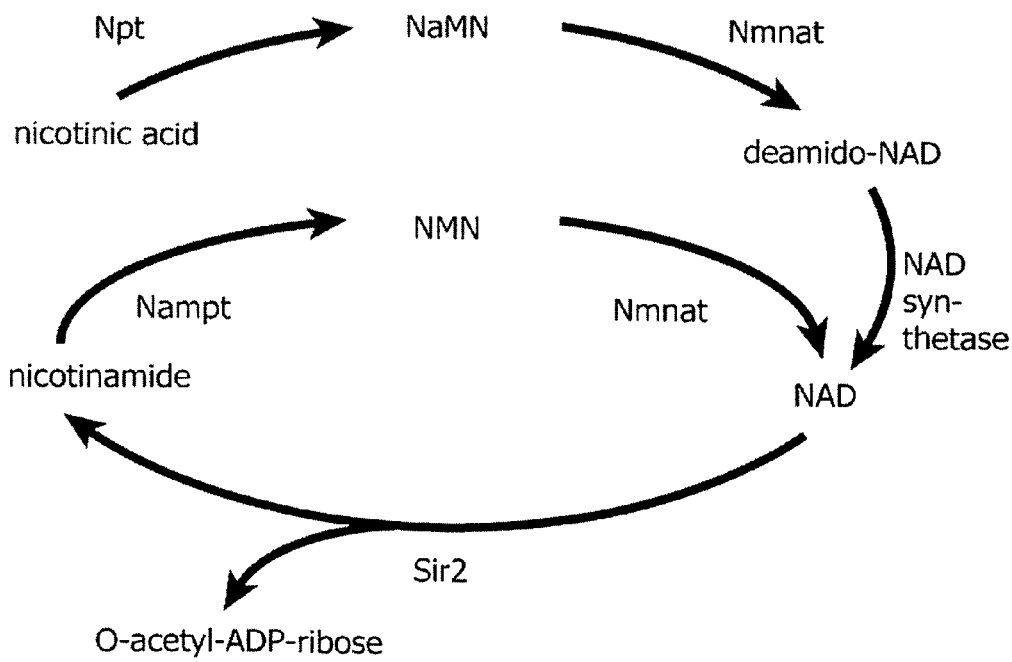
FIG. 1B shows NAD biosynthesis from nicotinamide and nicotinic acid in mammals. These pathways are also conserved throughout vertebrates. Nicotinamide is the main precursor for NAD biosynthesis in mammals. Npt, Nampt, and Nmnat are nicotinic acid phosphoribosyltransferase, nicotinamide phosphoribosyltransferase, and nicotinamide/nicotinic acid mononucleotide adenylyltransferase, respectively. NaMN, nicotinic acid mononucleotide; NMN, nicotinamide mononucleotide.

The NAD biosynthesis system was reconstituted in vitro with His-tagged recombinant enzymes. In mammals, NAD biosynthesis from nicotinamide is catalyzed by two enzymes, Nampt and Nmnat (FIG. 1B). Full-length cDNAs of the mouse Nampt and Nmnat genes were isolated from a mouse liver cDNA library by PCR.

Mouse Nampt cDNA was isolated based on a homology search in the mouse EST database to the amino acid sequence of *Haemophilus ducreyi* Nampt (Martin et al., J. Bacteriol. (2001) 183, 1168-1174). Mouse Nmnat, an ortholog to the human NMNAT-1 gene, was previously cloned as a fusion gene from the slow Wallerian degeneration mutant mouse (Mack et al., Nat. Neurosci. (2001) 4, 1199-1206). The coding regions of mouse Nampt and Nmnat cDNAs were amplified from a mouse liver cDNA library (Clontech, Calif.) by PCR with PfuTurbo polymerase (Stratagene, Calif.). The following forward and reverse primers containing EcoRI sites were generated: SEQ ID NO:4, Nampt forward; SEQ ID NO:5, Nampt reverse; SEQ ID NO:6, Nmnat forward; and SEQ ID NO:7, Nmnat reverse. The resulting 1584-bp and 972-bp fragments of Nampt and Nmnat cDNAs, respectively, were digested with EcoRI and cloned into the pBluescript SK-vector. Nampt and Nmnat cDNA fragments were then subcloned into the mammalian expression vector pCXN2 (Niwa et al., Gene (1991) 108, 193-199).

To create N-terminal His-tagged recombinant proteins of these two enzymes, Nampt and Nmnat cDNA fragments were re-amplified by PCR to create EcoRI and NdeI sites at the 5' ends of each cDNA, respectively. The PCR products were cloned into the pET-28a(+) vectors (EMD Biosciences, CA). To create expression vectors for Nampt and Nmnat proteins fused to GFP at their C-termini, the Nampt and Nmnat cDNA fragments were cloned between EcoRI and BamHI sites of the pEGFP-N1 vector (Clontech) after modifying their stop codons. All Nampt and Nmnat cDNA inserts were sequenced, and those sequences were deposited in the GenBank database as accession numbers AY679720 and AY679721, respectively. All necessary plasmids were prepared using the QIA-filter plasmid midi kit (Qiagen, CA).

To produce the recombinant proteins, BL21(DE3)pLysS cells were transformed with each of His-tagged Nampt and Nmnat plasmids. Transformed BL21 (DE3)pLysS cells were grown overnight at 37° C. in 25 ml of Terrific broth containing 75 μg/ml kanamycin and 37 μg/ml chloramphenicol. Cells were spun down, resuspended in 500 ml of the same media, and grown at 37° C. to an $OD_{600}$ of 0.6. His-tagged recombinant proteins were then induced by 1.5 mM isopropyl-D-thiogalactopyranoside (Sigma, Mo.). After inducing for 5 h at 37° C., cells were spun down and resuspended in lysis buffer (20 mM Tris-HCl [pH 8.0], 300 mM NaCl, 0.1% Triton X-100) with protease inhibitors (Roche Applied Science, IN) and lysozyme. The lysate was then produced with a French press and cleared at 10,000 g for 30 min. The His-tagged Nampt and Nmnat recombinant proteins were purified with Ni-NTA resin (Qiagen, CA) by washing with lysis buffer and wash buffer (20 mM Tris-HCl [pH 8.0], 300 mM NaCl, 10% glycerol, 0.1% Triton X-100, 40 mM imidazole) and eluting with 150 mM imidazole-containing buffer.

Figure 2A:
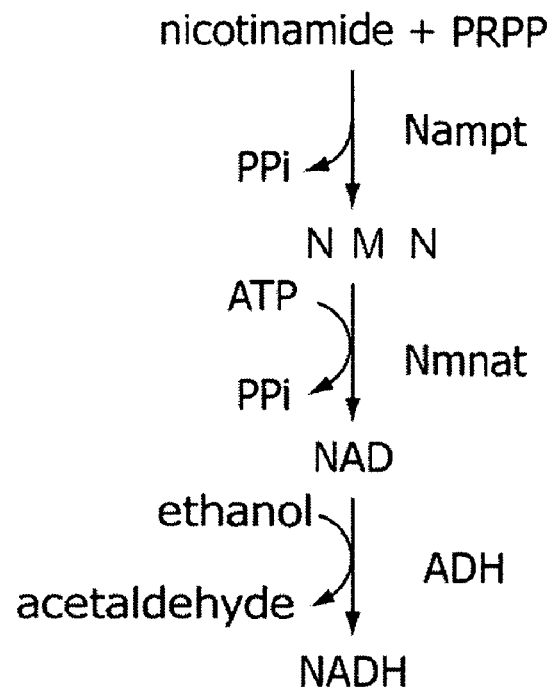
FIG. 2A shows the scheme of the NAD biosynthesis reactions in the enzyme-coupled fluorometric assay (see Example 2). The in vitro-synthesized NAD was converted to NADH by alcohol dehydrogenase (ADH), and the fluorescence of the resulting NADH was measured by a fluorometer. PRPP, phosphoribosyl pyrophosphate; PPi, inorganic pyrophosphate.
Figure 2B:
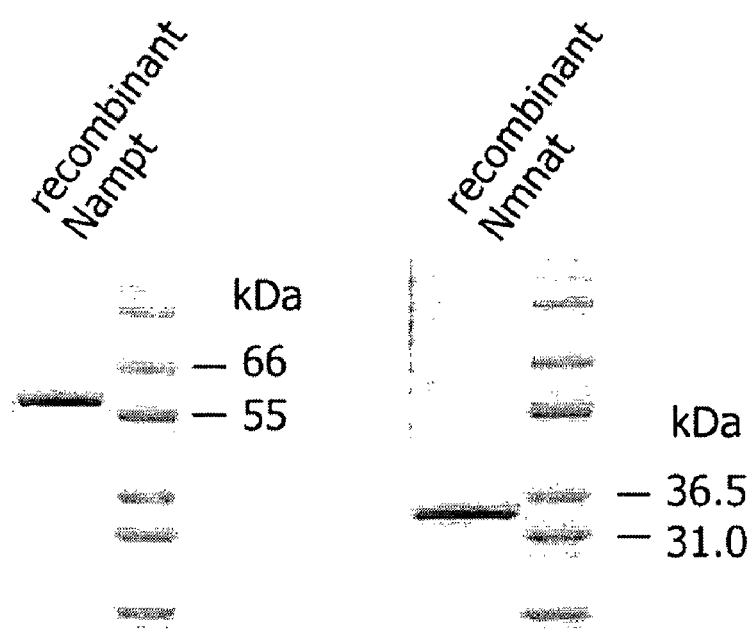
FIG. 2B depicts a gel upon which His-tagged recombinant polypeptides of mouse Nampt and Nmnat, produced in *E. coli*, were purified to homogeneity (see Example 1). One microgram of each polypeptide was electrophoresed and stained in SDS-PAGE gels.

Bacterially produced, His-tagged recombinant mouse Nampt and Nmnat proteins showed molecular weights of approximately 59 and 35 kDa, respectively, which are consistent with those predicted from their amino acid sequences (see e.g. FIG. 2B).

Example 2

Biochemical Characterization of Nampt and Nmnat

Enzymatic activities of recombinant Nampt and Nmnat proteins were measured by an enzyme-coupled fluorometric assay (see e.g. FIG. 2A). In this enzyme-coupled reaction, NAD is converted to NADH by alcohol dehydrogenase, and the fluorescence of NADH is detected in a fluorometer. To establish this assay system, optimal reaction conditions for Nmnat were initially examined by varying ATP and $Mg^{2+}$ concentrations and pH of the reaction buffer. The resultant reaction buffer for Nmnat contained 50 mM HEPES [pH 7.4], 0.02% BSA, 12 mM $MgCl_2$, 2 mM ATP, 1.5% ethanol, and 30 μg/ml alcohol dehydrogenase to convert NAD to NADH. To determine the kinetic parameters for Nmnat, 30 ng of purified His-tagged Nmnat and varying concentrations of NMN were added to 1 ml of the reaction buffer. The reactions were run at 37° C. and quenched at six time points by the addition of 250 μl of 0.5 M EDTA. The production of NADH was measured by excitation at 340 nm and emission at 460 nm in a fluorometer. For kinetic characterization of Nampt, 500 ng of His-tagged Nampt and varying concentrations of nicotinamide were reacted at 37° C. in 100 μl of a buffer containing 50 mM Tris-HCl [pH 7.5], 0.02% BSA, 12 mM $MgCl_2$, 2.5 mM ATP, 10 μg/ml His-tagged Nmnat, 0.4 mM phosphoribosyl pyrophosphate (PRPP), 1.5% ethanol, and 30 μg/ml alcohol dehydrogenase. NADH production was measured continuously in a fluorometer.

Figure 2C:
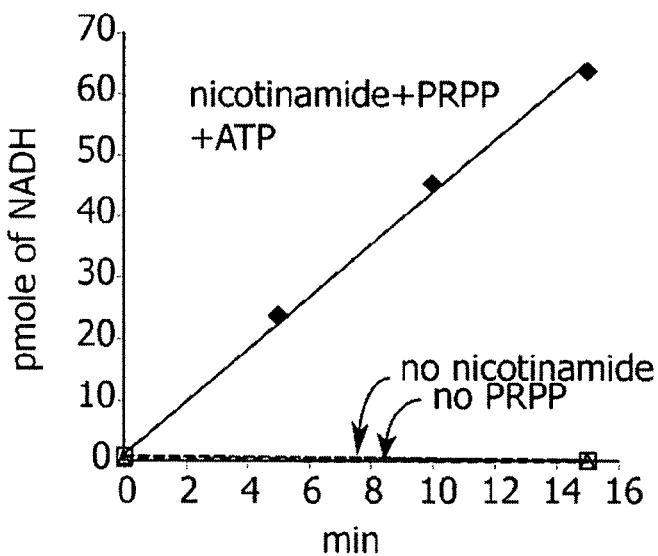
FIG. 2C is a graph showing production of NADH (pM) as a function of time (min) measured in the enzyme-coupled fluorometric assay using purified Nampt and Nmnat recombinant polypeptides (see Example 2). Filled squares indicate the reaction with nicotinamide, PRPP and ATP. Open squares and triangles indicate reactions without nicotinamide and PRPP, respectively.

Results showed that the in vitro-reconstituted NAD biosynthesis reaction generated NAD from nicotinamide, phosphoribosyl pyrophosphate (PRPP) and ATP (see e.g. FIG. 2C). No NAD was produced in the absence of nicotinamide or PRPP, the substrates of Nampt (see e.g. FIG. 2C).

Figure 3A:
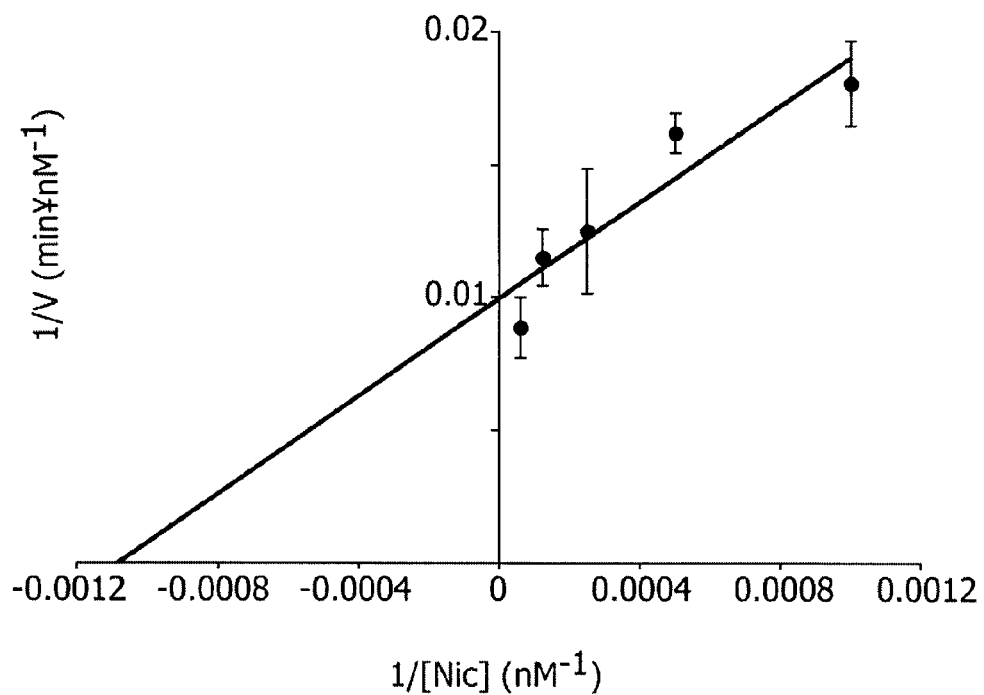
FIG. 3 is a line and scatter point graph that depicts Lineweaver-Burk plots of mouse Nampt (FIG. 3A) and Nmnat (FIG. 3B). Each data point and their standard deviations were determined by three independent assays (see Example 2). The $K_m$, $V_{max}$ and $k_{cat}$ for each enzyme calculated from these plots are shown in Table 1.
Figure 3B:
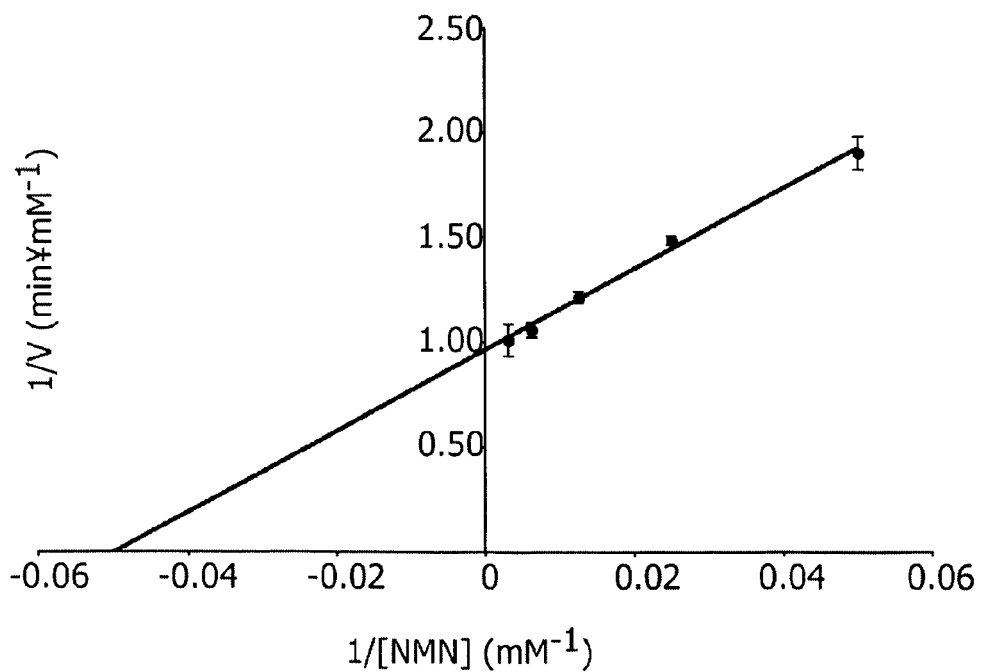

By using this enzyme-coupled fluorometric assay, kinetic parameters of purified recombinant mouse Nampt and Nmnat for nicotinamide and NMN, respectively, were determined (see e.g. Table 1). The Lineweaver-Burk plots for these two enzymes are shown, for example, in FIG. 3. Compared to reported kinetic parameters of other enzymes in the NAD biosynthesis pathways (Micheli and Sestini, Methods Enzymol. (1997) 280, 211-221), Nampt shows very high affinity for its substrate (Km=0.92 mM). The Km and Vmax of mouse Nmnat are consistent with previously reported values for human NMNAT-1 (Emanuelli et al., J. Biol. Chem. (2001) 276, 406-412). The catalytic efficiency of Nampt is ~46-fold less than that of Nmnat, suggesting that the reaction of Nampt is the rate-limiting step in the synthesis of NAD from nicotinamide.

Figure 2D:
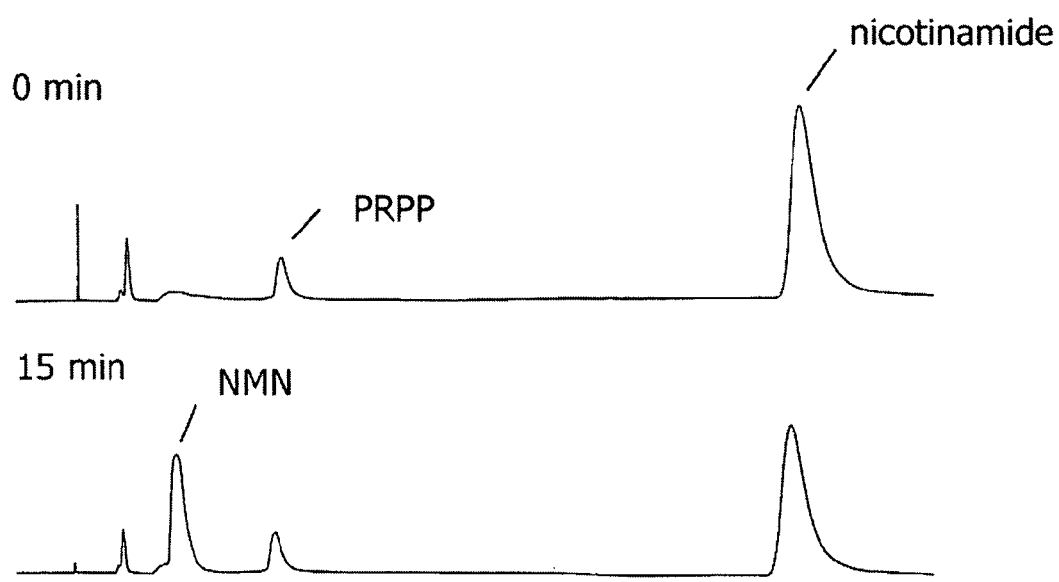
FIG. 2D depicts high performance liquid chromatography elutions of the products of mouse Nampt reaction (see Example 2). Chromatograms at 0 and 15 minute time points are shown. Elution times for each chemical were confirmed by running standards in the same HPLC conditions.
Figure 8A:
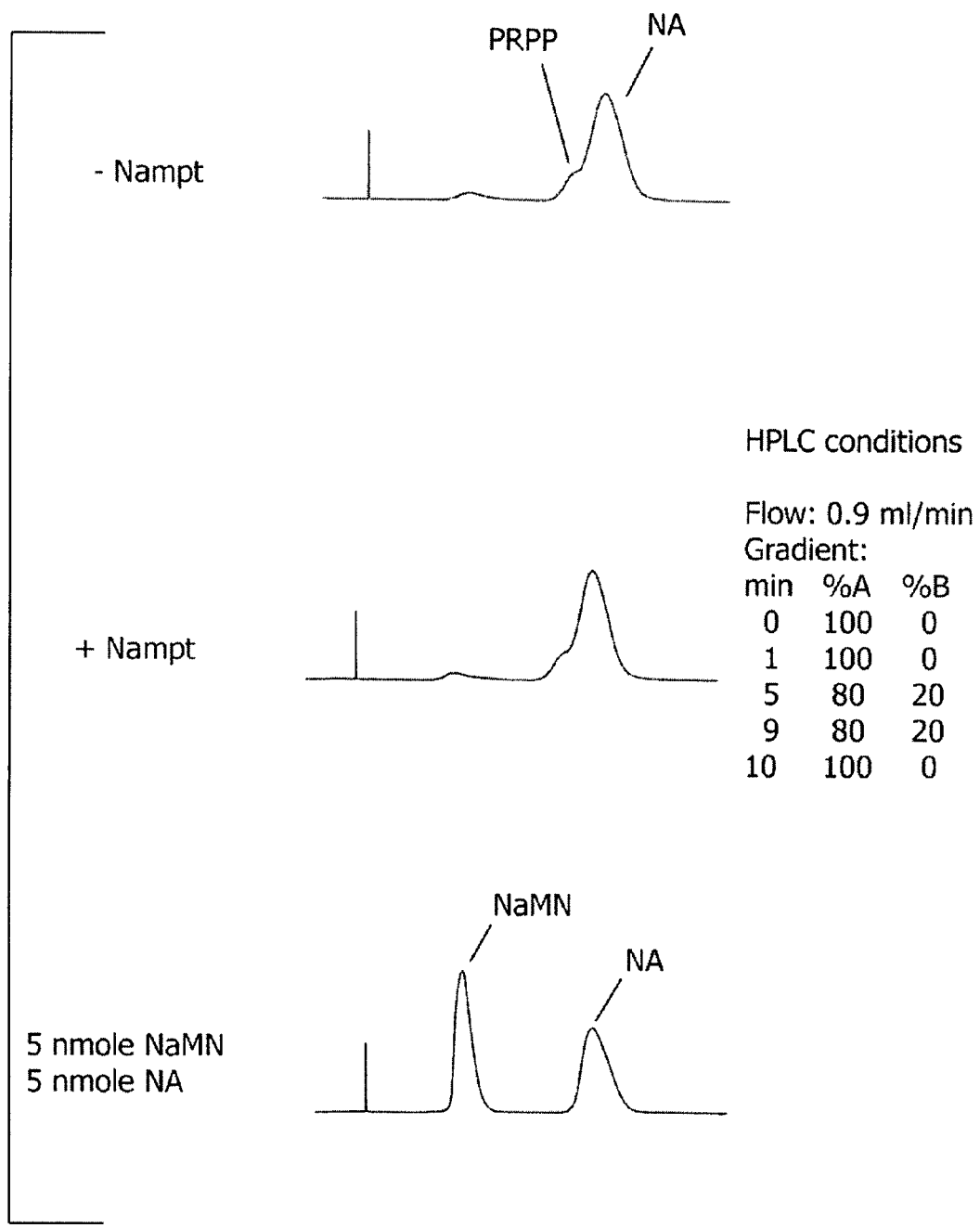
FIG. 8 is a series of HPLC elution traces demonstrating that Nampt does not catalyze the synthesis of nicotinic acid mononucleotide (NaMN) from nicotinic acid (NA) and phosphoribosyl pyrophosphate (PRPP). The Nampt reactions with nicotinic acid and nicotinamide (Nic) were conducted at 37° C. for 60 min in 500 ml of reaction buffer, and each reaction product was analyzed by HPLC (see Example 2). The flow rate and the gradient conditions for the detection of NaMN and NA are shown in the figure. While Nampt exhibited a robust synthesis of nicotinamide mononucleotide (NMN)
Figure 8B:
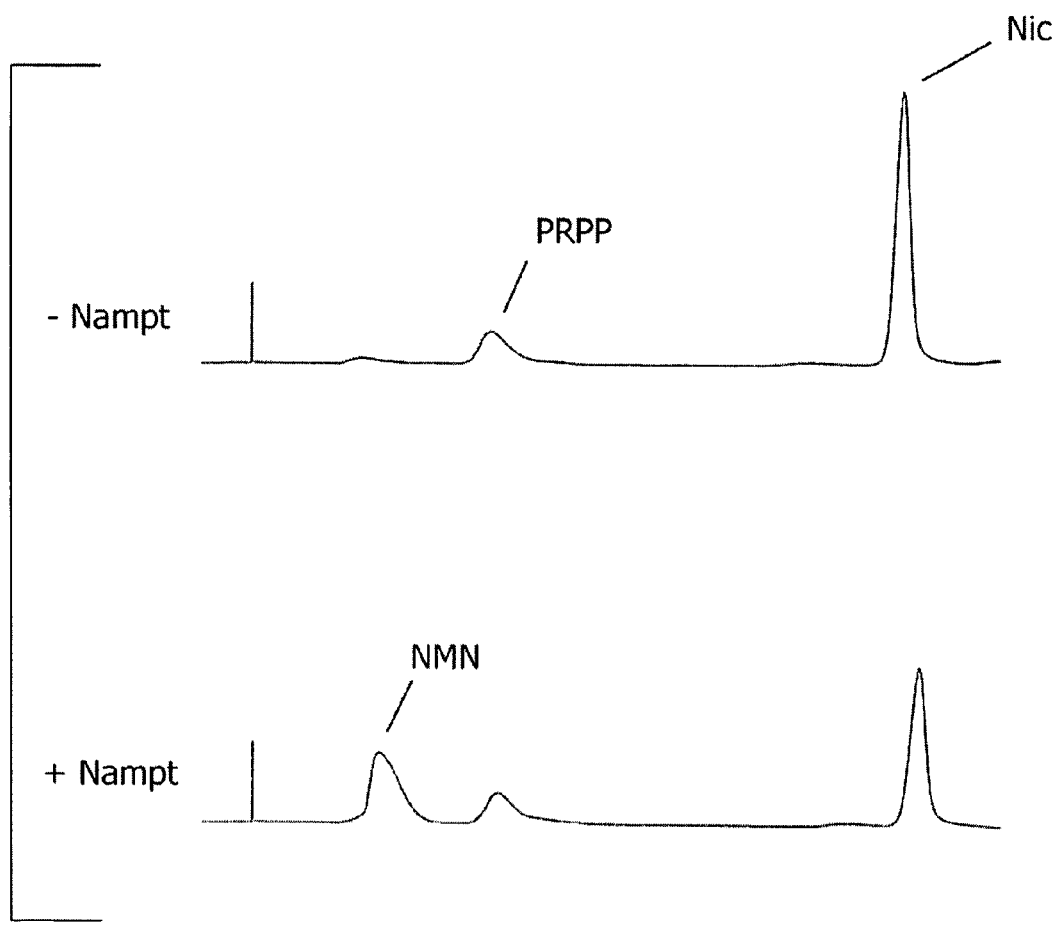

High performance liquid chromatography was used to detect Nampt reaction products. HPLC was performed with Waters 515 pumps and a 2487 detector (Waters, Mass.) with a Supelco LC-18-T column (15 cm×4.6 cm; Supelco, Pa.). The Nampt reaction was conducted at 37° C. for 15 min in 500 μl of reaction buffer (50 mM Tris-HCl [pH 7.5], 10 mM $MgCl_2$, 50 mM nicotinamide, 0.2 mM PRPP) with 50 μg of the recombinant Nampt protein. The reaction was terminated by adding 125 μl of 1 M $HClO_4$. Protein was then precipitated at 18,000 g, and 500 μL of the supernatant was neutralized with 40 μl of 3 M $K_2CO_3$. After centrifugation, 100 μl of sample was mixed with 400 μl of Buffer A (50 mM $K_2PO_4$/$KHPO_4$, pH 7.0) and loaded into the HPLC system. The products from Nampt reaction were monitored by absorbance at 261 nm. Results of HPLC detection of Nampt reaction products showed that the mouse Nampt produced nicotinamide mononucleotide (NMN) from nicotinamide and PRPP (see e.g. FIG. 2D). Nampt failed to catalyze the synthesis of nicotinic acid mononucleotide (NaMN) from nicotinic acid and PRPP (see e.g. FIG. 8), confirming the substrate specificity of this enzyme. In isolated reactions, it was also confirmed that Nmnat catalyzed the synthesis of NAD from NMN and ATP.

Example 3

Nampt Regulation of Cellular NAD Level in Mouse Fibroblasts

Because Nampt is the rate-limiting step in the mammalian NAD biosynthesis pathway starting from nicotinamide, increasing the dosage of Nampt increases total NAD levels in mammalian cells, as demonstrated with overexpression of the mouse Nampt gene in mouse NIH3T3 fibroblasts.

All NIH3T3 cell lines used in this study were established by selecting in the presence of 650-700 μg/ml of G418 (Invitrogen, Calif.). Approximately 1.2×10⁵ NIH3T3 cells were plated in 6 cm dishes. Transfection occurred as described above.

Polyclonal rabbit antisera were produced against the purified full-length His-tagged Nampt and Nmnat recombinant proteins (Covance, Pa.). Specific antibodies were affinity-purified from these antisera with HiTrap affinity columns (Amersham Biosciences, NJ) conjugated with each protein.

For Western Blotting, whole cell extracts were prepared with Laemmli's sample buffer. Proteins were separated in SDS-PAGE with 4-15% gradient or 12% gels and transferred onto Immobilon-P transfer membranes (Millipore, Mass.). Uniform transfer was confirmed by Ponceau S staining. Membranes were blocked in Tris-buffered saline with 0.1% Tween 20 (TBS-T buffer) and 5% dry milk (w/v) for 1 h at room temperature and washed three times in TBS-T. Membranes were blotted overnight at 4° C. with primary antibodies diluted at an appropriate dilution ratio in TBS-T with 5% dry milk and then with a secondary donkey anti-rabbit IgG antibody conjugated with horseradish peroxidase (Amersham Biosciences) for 1 h at room temperature. After washing, signals were developed with the ECL detection system (Amersham Biosciences).

Figure 4A:
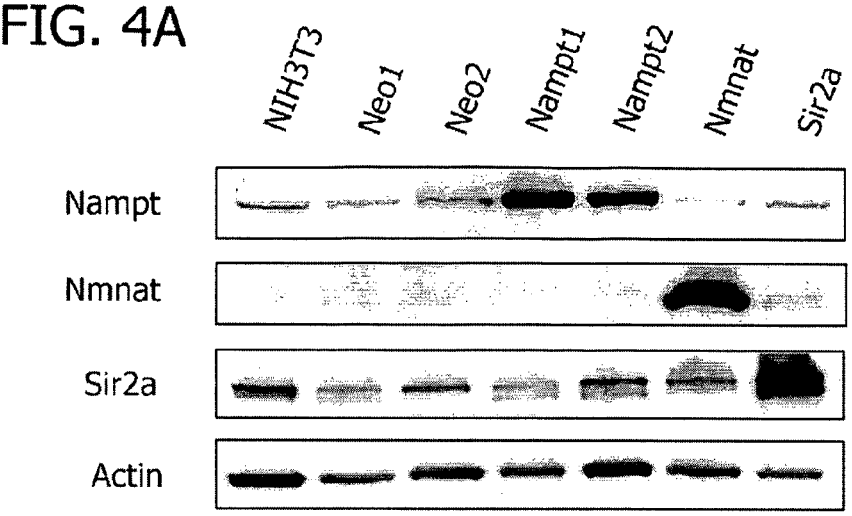
FIG. 4A is Western blot depicting enzyme expression of two Nampt-, one Nmnat- and one Sir2α-overexpressing NIH3T3 lines and two neomycin-resistant controls (see Example 3).

Results showed that in the original and neomycin-resistant control NIH3T3 cells, low amounts of the 56-kDa Nampt protein were detected with an affinity-purified rabbit polyclonal antibody raised against the recombinant full-length protein (see e.g. FIG. 4A). Two Nampt-overexpressing NIH3T3 cell lines, Nampt1 and 2, showed 23- to 15-fold higher amounts of the protein, respectively, compared to control neomycin-resistant cell lines, Neo1 and 2 (see e.g. FIG. 4A). The amounts of Nmnat did not change in these cell lines.

The mouse Nmnat and Sir2α genes in NIH3T3 cells was also overexpressed (see e.g. FIG. 4A). Nmnat (32 kDa) and Sir2α (apparent molecular weight 110 kDa) were detected with affinity-purified rabbit polyclonal antibodies against these proteins. Overexpression levels of Nmnat and Sir2α are approximately 14- and 4-fold, respectively. The amount of Nampt did not change in these cell lines. Using GFP-fusion expression vectors, it was also demonstrated that overexpressed Nmnat and Sir2α proteins were localized exclusively in the nucleus, while overexpressed Nampt protein was mainly localized in cytoplasm (see e.g. FIG. 9).

Total cellular levels of NAD was measured in the NIH3T3 cell lines overexpressing the untagged enzymes. High performance liquid chromatography was used to measure NAD (Neubert et al., Biochim. Biophys. Acta. (1964) 92, 610-612; Emanuelli et al., J. Chromatogr. (1996) B. 676, 13-18). Briefly, 5×10⁵ cells were plated in 6 cm dishes and harvested 48 h later in 800 µl of ice-cold PBS. Cells were then spun down and lysed with 300 µl of 1 M $HClO_4$ on ice for 10 min. Lysates were cleared by centrifugating at 4° C. at 18,000 g for 5 minutes. Cleared lysates (240 µl) were neutralized by adding 80 µl of 3M $K_2CO_3$ and incubating on ice for 10 minutes. After centrifuging for 10 min, 100 µl of the supernatant were mixed with 400 µl of Buffer A and loaded onto the column. The HPLC was run at a flow rate of 1 ml/min with 100% Buffer A from 0 to 5 min, a linear gradient to 95% Buffer A and 5% Buffer B (100% methanol) from 5 to 6 min, 95% Buffer A and 5% Buffer B from 6 to 11 min, a linear gradient to 85% Buffer A and 15% Buffer B from 11 to 13 min, 85% Buffer A and 15% Buffer B from 13 to 23 min, and a linear gradient to 100% Buffer A from 23 to 24 min. NAD was eluted as a sharp peak at 22 min. The amount of NAD was quantitated based on the peak area compared to a standard curve.

Figure 4B:
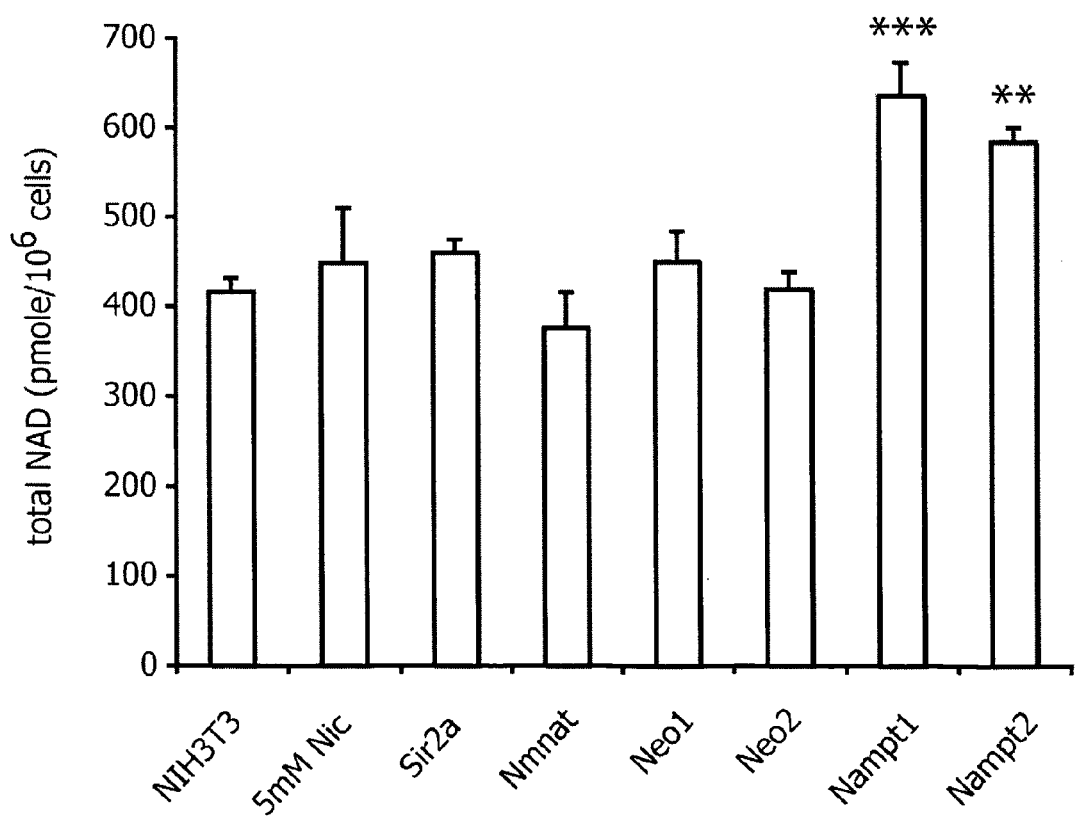
FIG. 4B depicts total cellular NAD levels in enzyme-overexpressing and nicotinamide-treated NIH3T3 cells as well as original NIH3T3 and neomycin-resistant controls. The averages and standard deviations were calculated from three to four independent assays and compared with one-way ANOVA and the Bonferroni multiple comparison test (see Example 3). Only Nampt-overexpressing cell lines (Nampt 1 and 2) show statistically significant increases in total cellular NAD levels. A triple asterisk indicates $P<0.001$. A double asterisk indicates $P<0.01$ or $0.001$.

Results showed that total NAD levels increased 47 and 35% in Nampt1 and 2 cell lines, respectively, compared to those in control cell lines (see e.g. FIG. 4B). In contrast, the total NAD levels did not change in cells overexpressing Nmnat or Sir2α (see e.g. FIG. 4B). Addition of 5 mM nicotinamide to the medium, which otherwise contains only 33 µM nicotinamide, did not increase NAD (see e.g. FIG. 4B). Consistent with the biochemical characteristics of these enzymes, these results suggest that Nampt is the rate-limiting component of the NAD biosynthesis pathway starting from nicotinamide in mouse fibroblasts.

Example 4

Nampt Effect on Sir2 Transcriptional Activity

A reporter gene transcription assay using a GAL4 DNA binding domain (GAL4 DBD) fusion system was developed to monitor the transcriptional regulatory activity of the mouse Sir2 ortholog, Sir2α. The GAL4 DBD system has been used extensively to evaluate the in vivo functions of mammalian histone deacetylases (Zhang et al., Cell (1997) 89, 357-364; Downes et al., Proc. Natl. Acad. Sci. USA (2000) 97, 10330-10335). This assay system used the GAL4 DBD fused to the Sir2α catalytic core domain (GAL4 DBD-mCORE) and a luciferase reporter that has a thymidine kinase minimal promoter and four GAL4 binding sites.

To make effector plasmids of mouse Sir2α for reporter gene transcription assays, the DNA fragments corresponding to amino acids 220-500 of the wild-type and mutant Sir2α (Luo et al., Cell (2001) 107, 137-148; Vaziri et al., Cell (2001) 107, 149-159) were amplified by PCR with PfuTurbo DNA polymerase (Stratagene) and primers that created EcoRI sites at both ends of each fragment. They were cloned into the EcoRI site of the pM mammalian expression vector (Clontech) to produce the N-terminal fusion to the GAL4 DNA binding domain. To make the expression vector for the C-terminally GFP-fused Sir2α protein, the Sir2α minigene that carries the 2.2-kbp Sir2α cDNA fragment, whose stop codon was modified, and a 1.3-kbp genomic fragment of the Sir2α gene upstream region was inserted between EcoRI and BamHI sites of the pEGFP-N1 vector after removing its CMV enhancer/promoter. The mouse Sir2α expression vector was pBabe-Sir2α.

Polyclonal rabbit anti-mouse Sir2α antiserum was raised against an N-terminal fragment (amino acid 1-131) of mouse Sir2α (Covance, Pa.). Specific antibodies were affinity-purified from this antisera with HiTrap affinity columns (Amersham Biosciences, NJ) conjugated with each protein.

For the luciferase assay, 1.2×10⁵ NIH3T3 cells were plated in 6 cm dishes. 24 h after plating, cells were transfected for 3 h with 380 ng of pUAS₄tk-luc as a reporter, 1.5 µg of pM or pM-GAL4 DBD-mCORE as an effector, and 38 ng of pRL-SV40 (Promega, Wis.) as a normalization control by using Superfect (Qiagen). Transfectants were harvested 48 h after transfection, and luciferase activity was measured with the Dual-Luciferase Reporter Assay System (Promega, Wis.) and a SIRIUS luminometer (Berthold Detection Systems, Germany) according to the manufacturers' protocols. Background luminescence was subtracted and was always less than 1% of measured values. Transfection efficiencies were normalized based on *Renilla* luciferase activities. 5 mM nicotinamide and 5 mM nicotinic acid were added 24 h after transfection. To examine the effects of Nampt and Nmnat on the transcriptional repressive activity of GAL4 DBD-mCORE, NIH3T3 cells were co-transfected with indicated amounts of Nampt and Nmnat expression vectors along with reporter, effector and normalization control plasmids.

Figure 5A:
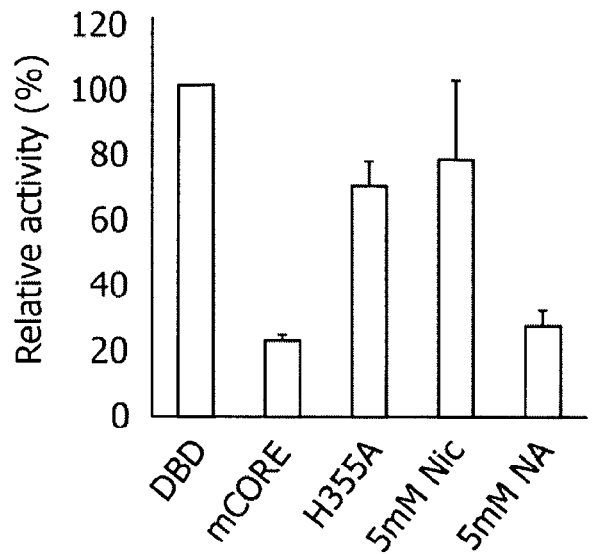
FIG. 5A is a bar graph showing transcriptional repressive activity of a GAL4 DNA binding domain fused to the Sir2α catalytic core domain (GAL4 DBD-mCORE) recruited onto GAL4 binding sites in the promoter of a luciferase reporter gene (see Example 4). Transfection efficiencies were normalized to *Renilla* luciferase activities, and the luciferase activity in the presence of GAL4 DBD (DBD) was assigned as 100%. The H355A point mutation and 5 mM nicotinamide (Nic), but not 5 mM nicotinic acid (NA), abolished the transcriptional repressive activity of GAL4 DBD-mCORE in this system. The averages and standard deviations shown were calculated from three independent assays.
Figure 5B:
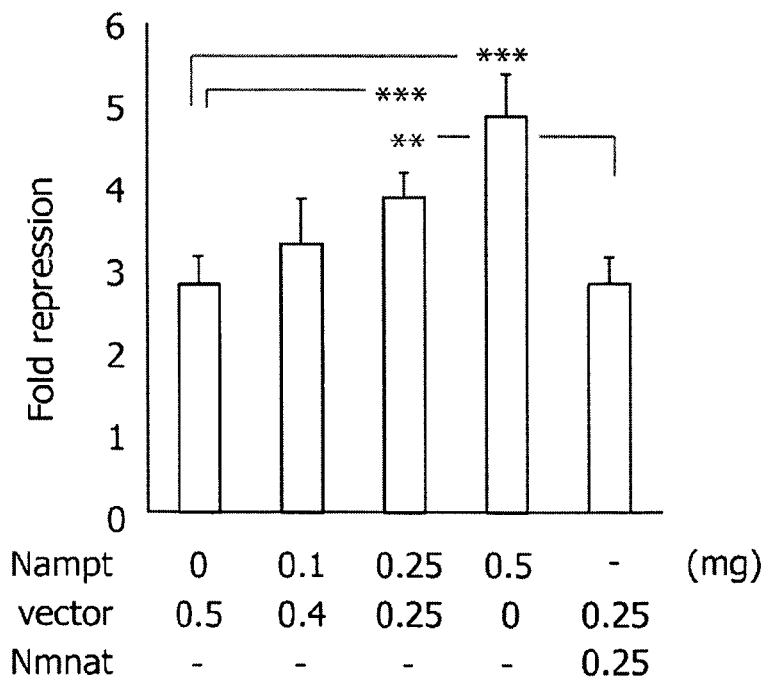
FIG. 5B is a bar graph depicting transcriptional repressive activity of GAL4 DBD-mCORE as a function of transient overexpression of Nampt and Nmnat. Luciferase activity was measured in NIH3T3 cells co-transfected with the reporter, pM-GAL4 DBD-mCORE, and indicated amounts of Nampt, Nmnat and/or control expression vectors (see Example 4). Fold repression was determined relative to the transcriptional activity of the reporter in the presence of GAL4 DBD. The averages and standard deviations from three to eleven independent assays were compared with one-way ANOVA and the Bonferroni multiple comparison test. A double asterisk indicates $P<0.01$. A triple asterisk indicates $P<0.001$.

Results showed that the GAL4 DBD-mCORE significantly repressed transcription compared to the activity of the GAL4 DBD control (see e.g. FIG. 5A). When the H355A mutation, which destroys more than 90% of the NAD-dependent deacetylase activity of Sir2α (Vaziri et al., Cell (2001) 107, 149-159) was introduced to the core domain, this repression was abolished (see e.g. FIG. 5A), demonstrating that the NAD-dependent deacetylase activity is correlated with this repressive activity. The repressive activity of GAL4 DBD-mCORE was also abolished by the addition of 5 mM nicotinamide, a chemical inhibitor for Sir2, but not by 5 mM nicotinic acid (see e.g. FIG. 5A), which further confirms that this system measures Sir2 activity.

The effect of the increased Nampt dosage on the transcriptional repressive activity of GAL4 DBD-mCORE was examined using this reporter assay. Results showed that transient co-transfection of the Nampt gene enhanced the repressive activity of GAL4 DBD-mCORE in a dose-dependent manner (see e.g. FIG. 5B). In contrast, transient co-transfection of the Nmnat gene did not enhance the activity of GAL4 DBD-mCORE (see e.g. FIG. 5B), consistent with the result that overexpression of Nmnat did not increase NAD (see e.g. FIG. 4B). Co-transfection of both Nampt and Nmnat genes also failed to increase the repressive activity of GAL4 DBD-mCORE beyond the effect of the Nampt gene alone.

Figure 5C:
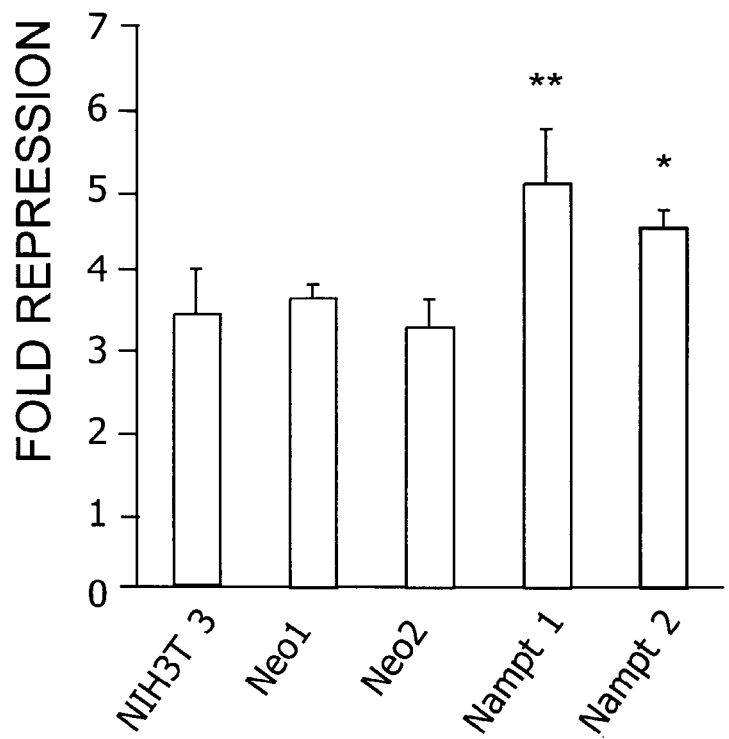
FIG. 5C is a bar graph depicting the transcriptional repressive activity of GAL4 DBD-mCORE in stable NIH3T3 cell lines overexpressing Nampt. Results from four independent assays were compared as described above (see Example 4). A double asterisk indicates $P<0.01$ or $0.001$. A single asterisk indicates $P<0.01$ or $0.05$.
Figure 5D:
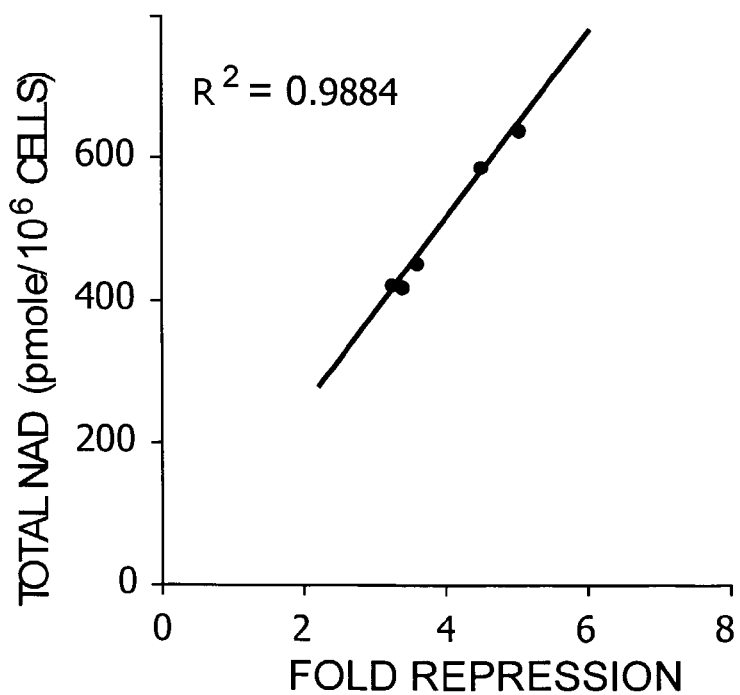
FIG. 5D is a scatter plot with a regression line depicting the correlation between total cellular NAD levels and transcriptional repressive activities of GAL4 DBD-mCORE. Data plotted in this figure were taken from FIGS. 4B and 5C.

Also measured was the repressive activity of GAL4 DBD-mCORE in the stable Nampt-overexpressing NIH3T3 cell lines, Nampt1 and 2. In these cell lines, the repressive activity of GAL4 DBD-mCORE was significantly enhanced (see e.g. FIG. 5C). Further, a correlation was observed between the total cellular NAD levels and the repressive activities of GAL4 DBD-mCORE in control and Nampt-overexpressing NIH3T3 cell lines (see e.g. FIG. 5D). Taken together, these results suggest that the increased dosage of Nampt enhances the transcriptional regulatory activity of Sir2α through the increase of total cellular NAD levels in mammalian cells.

Example 5

Nampt and Sir2 Induction of Gene Expression in Fibroblasts

Gene expression profiles between Nampt- and Sir2α-overexpressing NIH3T3 cells (Nampt1 and Sir2α; see FIG. 4) were compared by oligonucleotide microarrays with dye-swaps. Combining dye-swaps and strict filtering criteria allow reproducible detection of gene expression changes with ratios as low as 1.2-fold (Miller et al., Cancer Cell (2002) 2, 353-361). The gene expression profiles of Nampt- and Sir2α-overexpressing cell lines were independently determined in comparison to a neomycin-resistant control, Neo1, as illustrated in FIG. 6A. Experiments were repeated with biologically duplicated samples.

RNA samples were purified from Nampt-overexpressing (Nampt1), Sir2α-overexpressing (Sir2α) and neomycin-resistant control (Neo1) NIH3T3 cell lines by using an RNeasy kit (Qiagen) according to the manufacturer's protocol. The quality of RNA was examined by capillary electrophoresis. Eight micrograms of total RNA from each of the NIH3T3 cell lines were converted to cDNA by using the 3DNA Array 350 Expression Array Detection Kit (Genisphere, Pa.) according to the manufacturer's protocol. Microarray hybridization was then conducted with Cy3- and Cy5-labeled dendrimers as described (Scearce et al., Diabetes (2002) 51, 1997-2004) with the following modifications. Hybridization was conducted at 42° C. for 18 h in MWG Coverslips Hybridization Buffer (MWG USA, NC), and all post-hybridization washes were carried out at 25° C. To increase the accuracy of the microarray analysis, dye-swap experiments were performed for each pair of cell lines (Nampt1 vs. Neo1 and Sir2α vs. Neo1). Microarray hybridizations were performed in duplicate for each pair with the exception that the Cy3-Cy5 labeling scheme was swapped between hybridizations, i.e., (control-Cy3, experimental-Cy5) and (experimental-Cy5, control-Cy3) (see e.g. FIG. 6A). Including dye-swaps, four microarray slides were used for each pair-wise comparison. A ScanArray Express HT scanner and accompanying software (PerkinElmer, Mass.) was used to scan the slides and analyze the raw data, including normalization according to the Lowess method (Yang et al., Nucleic Acids Res. (2002) 30, e15). Spots used for statistical analysis satisfied the following criteria on at least three of the slides for both sets of comparisons: (1) ScanArray Express flag=3, (2) Signal to noise ratio $\geq 2$ in both channels. Spot-specific dye bias was corrected by subtracting a correction factor from the $\log_2$ of the Lowess-normalized median of ratios in the Cy5 and Cy3 channels. It has been reported that combining dye swapping and filtering out spots with signal intensities near background enables highly reproducible detection of gene expression changes with ratios as low as 1.2-fold (Miller et al., Cancer Cell (2002) 2, 353-361), which was confirmed in preliminary microarray experiments. Therefore, genes determined to be changed exhibited at least 1.2-fold differences between experimental and control cell lines with 95% confidence intervals that did not overlap the fold change of 1.

For Quantitative real-time RT-PCR, total RNA samples were purified as described above. For each sample, cDNA was synthesized from 10 µg of total RNA using an Omniscript kit (Qiagen) with random hexamer primers and RNase inhibitor (Promega) according to the manufacturer's protocol. The real-time quantitative RT-PCR was carried out in an ABI PRISM 7700 Sequence Detection System (Applied Biosystems) with a SYBR Green PCR Master Mix kit (Applied Biosystems) and gene-specific primers. Briefly, 2 µl of cDNA template (comparable to 200 ng of total RNA) were added to each well in a 96-well reaction plate, and the transcripts of each gene were amplified in triplicate. Average $C_T$ values were calculated, and the $\Delta C_T$ relative to GAPDH control were computed for each gene. Subsequently, $\Delta\Delta C_T$ was computed for each gene by subtracting the average $\Delta C_T$ for Nampt1-NIH3T3 cell lines from the average $\Delta C_T$ for the Neo1 control. The final fold differences were computed as $2^{-\Delta\Delta C_T}$ for each gene. The measurements were repeated three times with three independent RNA samples for each gene.

The gene expression profiles of Nampt- and Sir2α-overexpressing cell lines in comparison to a neomycin-resistant control, Neo1, are illustrated, for example, in FIG. 6A. Experiments were repeated with biologically duplicated samples. As shown, for example, in FIG. 6B, the gene expression profiles of Nampt- and Sir2α-overexpressing cells are significantly correlated (R=0.5617, $P \leq 6.359 \times 10^{-13}$), suggesting that increased dosage of Nampt enhances the transcriptional regulatory function of endogenous Sir2α in mouse fibroblasts. From a total of 9746 unique genes reliably detected in all three cell lines, 171 and 982 genes showed $\geq 1.2$-fold expression changes with 95% confidence in Nampt- and Sir2α-overexpressing cell lines, respectively (see e.g. FIG. 6C). 44 genes overlapped between these two groups ($P < 2 \times 10^{-9}$), and 36 of these genes showed the same directions of expression changes, listed in Table 2.

TABLE 2

Genes up- and down-regulated in both Nampt- and Sir2α-overexpressing cells.

| Genbank Accession | Name | Symbol | Nampt fold change | Nampt stdev | Sir2 fold change | Sir2 stdev |
|---|---|---|---|---|---|---|
| D90225 | pleiotrophin | Ptn | −1.92 | 0.18 | −3.43 | 0.17 |
| NM_008987 | pentaxin related gene | Ptx3 | −1.34 | 0.15 | −3.93 | 0.76 |
| NM_007913 | early growth response 1 | Egr1 | −2.08 | 0.75 | −2.71 | 0.80 |
| NM_008176 | chemokine (C—X—C motif) ligand 1 | Cxcl1 | −1.27 | 0.09 | −2.96 | 0.06 |
| AK010675 | serum amyloid A 3 | Saa3 | −1.24 | 0.05 | −2.09 | 0.43 |
| AK007378 | RIKEN cDNA 1810008K03 gene | 1810008K03Rik | −1.28 | 0.13 | −2.04 | 0.30 |
| K02782 | complement component 3 | C3 | −1.21 | 0.07 | −2.02 | 0.29 |
| NM_009117 | serum amyloid A 1 | Saa1 | −1.22 | 0.05 | −1.79 | 0.32 |
| L04694 | chemokine (C-C motif) ligand 7 | Ccl7 | −1.22 | 0.04 | −1.77 | 0.09 |
| NM_011415 | snail homolog 2 (*Drosophila*) | Snai2 | −1.33 | 0.17 | −1.59 | 0.37 |
| NM_007836 | growth arrest and DNA-damage-inducible 45 alpha | Gadd45a | −1.23 | 0.12 | −1.63 | 0.17 |
| AF128835 | polyadenylate binding protein-interacting protein 1 | Paip1 | −1.28 | 0.10 | −1.47 | 0.18 |
| AF328907 | stromal interaction molecule 2 | Stim2 | −1.33 | 0.12 | −1.39 | 0.13 |
| AK020727 | RIKEN cDNA A330102H22 gene | A330102H22Rik | −1.40 | 0.24 | −1.26 | 0.09 |
| AF357494 | unknown | | −1.32 | 0.06 | −1.27 | 0.12 |
| NM_008321 | inhibitor of DNA binding 3 | Idb3 | −1.24 | 0.08 | −1.34 | 0.12 |
| AK020270 | activating transcription factor 6 | Atf6 | −1.20 | 0.02 | −1.34 | 0.04 |
| AK013649 | RIKEN cDNA 2900045N06 gene | 2900045N06Rik | −1.23 | 0.09 | −1.27 | 0.12 |
| AK005117 | Adult male cerebellum cDNA | | 1.22 | 0.10 | 1.24 | 0.23 |
| AK016238 | unknown | | 1.25 | 0.08 | 1.22 | 0.21 |
| NM_026473 | RIKEN cDNA 2310057H16 gene | 2310057H16Rik | 1.21 | 0.04 | 1.31 | 0.07 |
| Z12572 | unknown | | 1.24 | 0.13 | 1.34 | 0.35 |
| AK019844 | Adult male testis cDNA | | 1.20 | 0.06 | 1.39 | 0.41 |
| AK013967 | RIKEN cDNA 4933434L15 gene | 4933434L15Rik | 1.25 | 0.09 | 1.35 | 0.38 |
| AK015276 | Adult male testis cDNA | | 1.38 | 0.10 | 1.23 | 0.24 |
| AK007471 | insulin induced gene 1 | Insig1 | 1.23 | 0.12 | 1.41 | 0.37 |
| AK003884 | protein phosphatase 1F (PP2C domain containing) | Ppm1f | 1.24 | 0.06 | 1.43 | 0.28 |
| AK021280 | gamma-aminobutyric acid (GABA-A) receptor, subunit alpha 2 | Gabra2 | 1.24 | 0.08 | 1.43 | 0.48 |
| NM_008006 | fibroblast growth factor 2 | Fgf2 | 1.29 | 0.15 | 1.38 | 0.18 |
| AF131212 | solute carrier family 29 (nucleoside transporters), member 1 | Slc29a1 | 1.20 | 0.09 | 1.50 | 0.07 |
| NM_025670 | RIKEN cDNA 5730403B10 gene | 5730403B10Rik | 1.34 | 0.17 | 1.42 | 0.33 |
| NM_013793 | killer cell lectin-like receptor, subfamily A, member 1 | Klra1 | 1.31 | 0.07 | 1.49 | 0.40 |
| NM_020581 | angiopoietin-like 4 | Angptl4 | 1.25 | 0.12 | 1.72 | 0.36 |
| AK017143 | 3 days neonate thymus cDNA | | 1.27 | 0.14 | 1.85 | 0.40 |
| NM_028133 | EGL nine homolog 3 (*C. elegans*) | Egln3 | 1.28 | 0.10 | 1.85 | 0.60 |
| D87034 | odd Oz/ten-m homolog 4 (*Drosophila*) | Odz4 | 1.20 | 0.09 | 2.00 | 0.57 |

The magnitude of the observed expression changes was higher in Sir2α-overexpressing cells (see e.g. Table 3) than in Nampt-overexpressing cells (see e.g. Table 4), consistent with the modest increase in total NAD levels and the transcriptional repressive activities of GAL4 DBD-mCORE in Nampt-overexpressing cells.

TABLE 3

Top 50 up- and down-regulated genes in Sir2α-overexpressing NIH3T3 cells

| Genbank Accession | Symbol | Fold change | St. Dev. |
|---|---|---|---|
| NM_007833 | Dcn | 9.03 | 1.94 |
| NM_018764 | Pcdh7 | 7.21 | 0.87 |
| NM_009369 | Tgfbi | 6.90 | 1.30 |
| AK019137 |  | 4.02 | 0.42 |
| AK011996 | 2610306H15Rik | 3.34 | 0.57 |
| NM_030554 | Rab27b | 3.06 | 0.38 |
| M11739 | Cck | 3.03 | 0.16 |
| NM_019867 | Ngef | 2.84 | 0.17 |
| NM_019922 | Crtap | 2.72 | 0.70 |
| NM_011845 | Mid2 | 2.71 | 0.67 |
| NM_010771 | Matr3 | 2.66 | 0.92 |
| NM_026214 | Kctd4 | 2.66 | 0.72 |
| AK003744 | Cst6 | 2.58 | 0.63 |
| AF192525 | Pscdbp | 2.50 | 0.74 |
| NM_009154 | Sema5a | 2.44 | 0.16 |
| AK017269 | 4933428A15Rik | 2.44 | 0.70 |
| NM_020332 | ank | 2.25 | 0.23 |
| NM_016719 | Grb14 | 2.23 | 0.61 |
| NM_009841 | Cd14 | 2.15 | 0.21 |
| NM_013496 | Crabp1 | 2.14 | 0.14 |
| AK004559 | Cpne8 | 2.11 | 0.44 |
| D87034 | Odz4 | 2.00 | 0.29 |
| AY005133 | 4932702G04Rik | 1.95 | 0.42 |
| AK013991 | 3110004L20Rik | 1.94 | 0.40 |
| AB059565 | Akr1c18 | 1.94 | 0.22 |
| NM_011923 | Angptl2 | 1.93 | 0.21 |
| NM_013519 | Foxc2 | 1.90 | 0.22 |
| U95030 | Alcam | 1.88 | 0.40 |
| NM_009121 | Sat1 | 1.87 | 0.12 |
| BC005558 | Ppap2b | 1.87 | 0.21 |
| NM_021465 | Stag2 | 1.86 | 0.23 |
| NM_028133 | Egln3 | 1.85 | 0.31 |
| AK017143 |  | 1.85 | 0.21 |
| AK003637 | 1110012J17Rik | 1.85 | 0.50 |
| AK012530 | Dusp4 | 1.80 | 0.11 |
| AL359935 | Adamts7 | 1.79 | 0.20 |
| NM_011581 | Thbs2 | 1.78 | 0.18 |
| BC003326 | Eif2b2 | 1.77 | 0.12 |
| U94828 | Rgs16 | 1.77 | 0.28 |
| NM_008537 | Amacr | 1.77 | 0.21 |
| NM_010441 | Hmga2 | 1.77 | 0.15 |
| AK006202 |  | 1.76 | 0.24 |
| NM_013465 | Ahsg | 1.75 | 0.29 |
| NM_009106 | Rtkn | 1.75 | 0.38 |
| NM_029392 |  | 1.75 | 0.13 |
| NM_009477 | Upp1 | 1.74 | 0.18 |
| AK011267 |  | 1.74 | 0.15 |
| AY029586 | 1010001D01Rik | 1.73 | 0.14 |
| AK009255 | D630041K24Rik | 1.73 | 0.02 |
| NM_020581 | Angptl4 | 1.72 | 0.19 |
| NM_007987 | Tnfrsf6 | −4.29 | 0.49 |
| NM_008987 | Ptx3 | −3.93 | 0.76 |
| NM_011580 | Thbs1 | −3.88 | 0.35 |
| D90225 | Ptn | −3.43 | 0.17 |
| K02109 | Fabp4 | −3.37 | 0.69 |
| AF407332 | Catsper1 | −3.10 | 0.43 |
| X68882 | Emx2 | −3.02 | 0.68 |
| NM_009141 | Cxcl5 | −2.98 | 0.26 |
| NM_008176 | Cxcl1 | −2.96 | 0.06 |
| NM_011598 | Fabp9 | −2.87 | 0.72 |
| NM_019764 | Amotl2 | −2.83 | 0.49 |
| AF206329 | Polydom | −2.74 | 0.68 |
| NM_007913 | Egr1 | −2.71 | 0.80 |
| NM_010217 | Ctgf | −2.67 | 0.34 |
| AJ131195 |  | −2.67 | 0.43 |
| AK008424 | 9430041O17Rik | −2.63 | 0.18 |
| NM_011693 | Vcam1 | −2.56 | 0.39 |
| AB031386 | 1810009M01Rik | −2.44 | 0.36 |
| AK007469 | 1810013B01Rik | −2.39 | 0.84 |
| NM_023852 | Rab3c | −2.38 | 0.21 |
| NM_010708 | Lgals9 | −2.36 | 0.28 |
| AK002480 |  | −2.32 | 0.31 |
| NM_010516 | Cyr61 | −2.31 | 0.34 |
| NM_009781 | Cacna1c | −2.26 | 0.75 |
| AK011583 |  | −2.24 | 0.56 |
| BC009087 | Smpdl3b | −2.21 | 0.54 |
| NM_010101 | Edg3 | −2.19 | 0.48 |
| U58881 | Ppp1r13b | −2.17 | 0.45 |
| AK007165 | 1700110N18Rik | −2.16 | 0.34 |
| X73016 | Igh-V | −2.15 | 0.71 |
| X14607 | Lcn2 | −2.12 | 0.26 |
| AK010675 | Saa3 | −2.09 | 0.43 |
| BC005647 | Brpf1 | −2.08 | 0.50 |
| L17333 | Ggt1 | −2.08 | 0.55 |
| AF132083 | Pthr2 | −2.06 | 0.38 |
| AK007378 | 1810008K03Rik | −2.04 | 0.30 |
| K02782 | C3 | −2.02 | 0.29 |
| NM_013468 | Ankrd1 | −2.02 | 0.34 |
| AF272146 | Fzd5 | −2.00 | 0.44 |
| AK013550 | Cdk5rap2 | −1.99 | 0.69 |
| NM_010330 | Emb | −1.98 | 0.04 |
| M96163 | Plk2 | −1.98 | 0.24 |
| AK009778 | Xrcc1 | −1.98 | 0.66 |
| NM_013618 | Olfr66 | −1.98 | 0.28 |
| NM_008627 | Mrg2 | −1.98 | 0.51 |
| NM_011315 | Saa3 | −1.97 | 0.43 |
| NM_011595 | Timp3 | −1.96 | 0.29 |
| NM_019759 | Dpt | −1.95 | 0.12 |
| AK017548 | Tle4 | −1.92 | 0.35 |
| AF148216 | C1r | −1.92 | 0.15 |

TABLE 4

Top 50 up- and down-regulated genes in Nampt-overexpressing NIH3T3 cells

| Genbank Accession | Symbol | Fold Change | St. Dev. |
|---|---|---|---|
| NM_018857 | Msln | 2.06 | 0.42 |
| BC006770 |  | 1.79 | 0.17 |
| AF244360 | Mpi1 | 1.50 | 0.30 |
| NM_009796 | Capn7 | 1.45 | 0.18 |
| AK014686 | BC042775 | 1.40 | 0.23 |
| AB048542 | Helb | 1.39 | 0.17 |
| AF260740 | Gpha2 | 1.39 | 0.04 |
| AK015276 |  | 1.38 | 0.10 |
| AK014582 | Arrdc2 | 1.38 | 0.22 |
| AK010408 |  | 1.37 | 0.19 |
| AK004796 |  | 1.35 | 0.03 |
| NM_008442 | Kif2a | 1.35 | 0.18 |
| NM_025670 | 5730403B10Rik | 1.34 | 0.17 |
| AK016511 |  | 1.34 | 0.19 |
| AY007815 | 9930013L23Rik | 1.34 | 0.14 |
| AK013779 | 2900074C18Rik | 1.33 | 0.13 |
| NM_011470 | Sprr2d | 1.33 | 0.06 |
| U95783 |  | 1.33 | 0.18 |
| AK016498 |  | 1.33 | 0.06 |
| AK010068 | Mfhas1 | 1.33 | 0.15 |
| BC005459 | Pls3 | 1.32 | 0.16 |
| AK014782 |  | 1.32 | 0.07 |
| AK013495 | 2900006N09Rik | 1.32 | 0.04 |
| NM_016659 | Klra1 | 1.32 | 0.17 |
| NM_013793 | Klra1 | 1.31 | 0.07 |
| NM_023630 | Gtf2a1lf | 1.31 | 0.12 |
| NM_010200 | Fgfl3 | 1.30 | 0.15 |

TABLE 4-continued

Top 50 up- and down-regulated genes in Nampt-overexpressing NIH3T3 cells

| Genbank Accession | Symbol | Fold Change | St. Dev. |
|---|---|---|---|
| AK016873 | BB075781 | 1.30 | 0.16 |
| NM_011607 | Tnc | 1.30 | 0.09 |
| BC005641 | 1810073N04Rik | 1.29 | 0.08 |
| NM_008006 | Fgf2 | 1.29 | 0.15 |
| AF283252 | Klra12 | 1.28 | 0.05 |
| AF183960 | Ccrn4l | 1.28 | 0.11 |
| AK005856 | | 1.28 | 0.10 |
| NM_028133 | Egln3 | 1.28 | 0.10 |
| AL357197 | 8030499H02Rik | 1.28 | 0.15 |
| AK015845 | 4930519L02Rik | 1.27 | 0.16 |
| AK018583 | 2010005J08Rik | 1.27 | 0.14 |
| AK017143 | | 1.27 | 0.14 |
| AK013971 | Tex261 | 1.27 | 0.15 |
| BC006046 | 4931426K16Rik | 1.26 | 0.14 |
| AF126834 | Ppl | 1.26 | 0.10 |
| AF326313 | Pcdhb20 | 1.26 | 0.09 |
| NM_008377 | Lrig1 | 1.25 | 0.07 |
| NM_009356 | Tesp2 | 1.25 | 0.08 |
| Z12576 | | 1.25 | 0.14 |
| AK019614 | | 1.25 | 0.09 |
| NM_020581 | Angptl4 | 1.25 | 0.12 |
| AK017449 | | 1.25 | 0.06 |
| NM_019759 | Dpt | 1.25 | 0.07 |
| NM_007913 | Egr1 | −2.08 | 0.75 |
| D90225 | Ptn | −1.92 | 0.18 |
| X56565 | Rara | −1.78 | 0.13 |
| AK007847 | D15Mit260 | −1.57 | 0.26 |
| NM_007897 | Ebf1 | −1.48 | 0.23 |
| NM_028756 | Slc35a5 | −1.47 | 0.26 |
| AK020051 | Npn1 | −1.46 | 0.23 |
| AK008822 | 4933404O11Rik | −1.45 | 0.17 |
| AF240500 | | −1.45 | 0.18 |
| AF176529 | Fbxo13 | −1.42 | 0.16 |
| NM_011999 | Clecsf6 | −1.41 | 0.06 |
| AK018526 | 9030425C21Rik | −1.40 | 0.19 |
| AK020727 | A330102H22Rik | −1.40 | 0.24 |
| NM_025422 | 1110055L24Rik | −1.39 | 0.15 |
| AA733351 | Atp5k | −1.38 | 0.19 |
| NM_010496 | Idb2 | −1.38 | 0.16 |
| NM_009069 | Rit1 | −1.38 | 0.18 |
| NM_007901 | Edg1 | −1.38 | 0.20 |
| AB010322 | | −1.37 | 0.06 |
| NM_015772 | Sall2 | −1.37 | 0.12 |
| AK005108 | 1500011L16Rik | −1.36 | 0.18 |
| AK018143 | Cgn | −1.35 | 0.17 |
| NM_008987 | Ptx3 | −1.34 | 0.15 |
| NM_010603 | Kcnj12 | −1.34 | 0.19 |
| AK010523 | | −1.33 | 0.15 |
| NM_011415 | Snai2 | −1.33 | 0.17 |
| X73017 | | −1.33 | 0.11 |
| AK019756 | 4930550B20Rik | −1.33 | 0.09 |
| NM_007834 | Dscr3 | −1.33 | 0.12 |
| AF328907 | Stim2 | −1.33 | 0.12 |
| NM_009102 | Rrh | −1.33 | 0.12 |
| AF357494 | | −1.32 | 0.06 |
| AK017929 | Zfp198 | −1.32 | 0.10 |
| M32376 | Igh-VJ558 | −1.31 | 0.18 |
| AK021172 | C330002I19Rik | −1.31 | 0.16 |
| AK017485 | | −1.31 | 0.12 |
| NM_013599 | Mmp9 | −1.30 | 0.13 |
| M19899 | Igh-VJ558 | −1.30 | 0.11 |
| BC005799 | Depdc1 | −1.30 | 0.13 |
| AF190624 | Ypel1 | −1.30 | 0.15 |
| AK012993 | | −1.29 | 0.15 |
| NM_025368 | 1110007C05Rik | −1.29 | 0.15 |
| Y13560 | | −1.29 | 0.12 |
| AK013637 | 2900042E01Rik | −1.29 | 0.09 |
| NM_007993 | Fbn1 | −1.29 | 0.12 |
| NM_025682 | Pspc1 | −1.29 | 0.14 |
| J00418 | | −1.29 | 0.10 |
| NM_026034 | 2810037C14Rik | −1.29 | 0.14 |
| AK018356 | | −1.28 | 0.15 |
| NM_008378 | Impact | −1.28 | 0.14 |

The accuracy of microarray measurements was confirmed for representative genes with quantitative real-time RT-PCR (see e.g. FIGS. 6D and 6E). Consistent with the results from NAD measurements and reporter gene transcription assays, these results demonstrate that NAD biosynthesis regulated by Nampt controls Sir2α activity in mammalian cells.

What is claimed is:

1. An aqueous solution for the in-vitro biosynthesis of reduced nicotinamide adenine dinucleotide (NADH) comprising:
   a nicotinamide phosphoribosyltransferase (Nampt) polypeptide at a concentration of about 0.01 μg/mL to about 100 μg/mL;
   a mammalian nicotinamide mononucleotide adenylyltransferase (Nmnat) polypeptide at a concentration of about 0.01 μg/mL to about 200 μg/mL;
   alcohol dehydrogenase protein (ADH);
   bovine serum albumen (BSA);
   ATP;
   phosphoribosyl pyrophosphate (PRPP);
   a magnesium ion;
   ethanol; and
   a buffer selected from the group consisting of HEPES and Tris, wherein the Nampt and the Nmnat are each at least partially purified from other cellular constituents.

* * * * *